United States Patent
Yamamoto et al.

(12)

(10) Patent No.: US 6,841,719 B1
(45) Date of Patent: *Jan. 11, 2005

(54) PLANT VDE GENES AND METHODS RELATED THERETO

(76) Inventors: Harry Y. Yamamoto, 716 Paoo St., Honolulu, HI (US) 96825; Robert C. Bugos, 2135 Chamberlain St., Honolulu, HI (US) 96822; David C. Rockholm, 1704 Anapuni St., Honolulu, HI (US) 96822

(*) Notice: Subject to any disclaimer, the term of this patent is extended or adjusted under 35 U.S.C. 154(b) by 0 days.

This patent is subject to a terminal disclaimer.

(21) Appl. No.: 09/075,375

(22) Filed: May 7, 1998

Related U.S. Application Data

(63) Continuation-in-part of application No. 08/747,574, filed on Nov. 7, 1996, now Pat. No. 6,015,939.
(60) Provisional application No. 60/023,502, filed on Aug. 6, 1996, and provisional application No. 60/006,315, filed on Nov. 7, 1995.
(51) Int. Cl.[7] .................. C12N 15/29; C12N 15/82; A01H 5/00
(52) U.S. Cl. .................. 800/282; 800/278; 800/298
(58) Field of Search .................. 800/278, 298, 800/285, 286, 282, 279; 536/23.1, 23.2, 23.6, 24.5; 435/69.1, 172.3, 410, 411

(56) References Cited

U.S. PATENT DOCUMENTS 6,015,939 A * 1/2000 Yamamoto et al. ......... 800/278

OTHER PUBLICATIONS

Napoli et al. The Plant Cell. 1989. Vol. 2: 278–289.*

Tepperman et al. Plant Molecular Biology. 1990. Vol. 14: 501–511.*

Colliver S.P. et al. Plant Mol. Biol. 1997; vol. 35, pp. 509–522.*

* cited by examiner

*Primary Examiner*—Amy J. Nelson
*Assistant Examiner*—Russell Kallis
(74) *Attorney, Agent, or Firm*—Grace L. Bonner

(57) ABSTRACT

DNA sequences encoding plant vde enzymes are provided herein. The sequences may be joined to heterologous DNA sequences for use as probes and in DNA constructs to modify the genotype of a host organism. DNA constructs and methods are provided to modify a host cell phenotype by altering the amount of photoprotection enzyme present in the host cell. In plastid containing host cells, zeaxanthin levels and sensitivity to light can be modified through alterations in the level of vde enzymes.

2 Claims, 23 Drawing Sheets

```
                                                        60
                                                         *
TGTGGGTTCG AATTTTACCC ACCACAAGTT TTGTCCTACC ATAATTGGGA TAAGGAGTCT
                                                        120
                                                         *
AATTTCCCTT GTACAATTTT CCAATTTCTT CCTCCGCCAC ACCATATATA TACTGTACGC
                                                        180
                                                         *
CACTTCGAAC GCTACAATGT TTGAAAAAAG ACGCAGATTT TACAAAGACG GAGAAGATAA

TAAGCTTCAA GTACTCCGAT CGTCAGGTGG CCTTTGGAAG CCAACAAACT GGCT ATG
                                                                Met
240
 *
GCT CTT TCT CTT CAC ACT GTA TTT CTC TGC AAA GAG GAA GCC CTC AAT
Ala Leu Ser Leu His Thr Val Phe Leu Cys Lys Glu Glu Ala Leu Asn

TTA TAT GCA AGA TCA CCA TGT AAT GAA AGG TTT CAC AGG AGT GGA CAA
Leu Tyr Ala Arg Ser Pro Cys Asn Glu Arg Phe His Arg Ser Gly Gln
               300
                *
CCT CCT ACC AAC ATA ATC ATG ATG AAA ATT CGA TCC AAC AAT GGA TAT
Pro Pro Thr Asn Ile Ile Met Met Lys Ile Arg Ser Asn Asn Gly Tyr
                                                        420
                                                         *
TTT AAT TCT TTC CGG TTG TTT ACA TCT TAT AAG ACA AGT TCT TTC TCA
Phe Asn Ser Phe Arg Leu Phe Thr Ser Tyr Lys Thr Ser Ser Phe Ser
```

FIGURE 1A

```
GAT TCT AGC CAT TGC AAG GAT AAA TCT CAG ATA TGC AGC ATC GAT ACA
Asp Ser Ser His Cys Lys Asp Lys Ser Gln Ile Cys Ser Ile Asp Thr
480
 *

AGT TTT GAG GAA ATA CAA AGA TTT GAT CTC AAA AGG GGC ATG ACT TTG
Ser Phe Glu Glu Ile Gln Arg Phe Asp Leu Lys Arg Gly Met Thr Leu
       540
        *

ATT CTT GAA AAG CAA TGG AGA CAA TTC ATA CAA TTG GCT ATC GTA TTG
Ile Leu Glu Lys Gln Trp Arg Gln Phe Ile Gln Leu Ala Ile Val Leu
              600
               *

GTT TGC ACA TTT GTT ATC GTT CCC AGA GTT GAT GCC GTT GAT GCT CTT
Val Cys Thr Phe Val Ile Val Pro Arg Val Asp Ala Val Asp Ala Leu
                          660
                           *

AAA ACT TGT GCT TGT TTA CTC AAA GAA TGC AGG ATT GAG CTT GCA AAA
Lys Thr Cys Ala Cys Leu Leu Lys Glu Cys Arg Ile Glu Leu Ala Lys

TGT ATA GCA AAC CCA TCT TGT GCG GCA AAC GTT GCC TGT CTA CAG ACT
Cys Ile Ala Asn Pro Ser Cys Ala Ala Asn Val Ala Cys Leu Gln Thr
720
 *

TGC AAC AAT CGT CCT GAC GAG ACC GAA TGT CAG ATA AAA TGT GGT GAC
Cys Asn Asn Arg Pro Asp Glu Thr Glu Cys Gln Ile Lys Cys Gly Asp
```

FIGURE 1B

```
            780
             *
TTG TTC GAA AAC AGT GTG GTG GAC CAA TTC AAC GAG TGT GCG GTT TCC
Leu Phe Glu Asn Ser Val Val Asp Gln Phe Asn Glu Cys Ala Val Ser
                                840
                                 *
CGA AAG AAA TGT GTG CCC CGG AAA TCG GAT GTG GGT GAA TTC CCG GTT
Arg Lys Lys Cys Val Pro Arg Lys Ser Asp Val Gly Glu Phe Pro Val
                                                900
                                                 *
CCG GAT CGT AAT GCA GTG GTT CAA AAT TTT AAC ATG AAA GAC TTT AGT
Pro Asp Arg Asn Ala Val Val Gln Asn Phe Asn Met Lys Asp Phe Ser

GGG AAG TGG TAT ATA ACA AGT GGT TTA AAT CCT ACA TTT GAT GCA TTT
Gly Lys Trp Tyr Ile Thr Ser Gly Leu Asn Pro Thr Phe Asp Ala Phe
 960
  *
GAT TGT CAA CTT CAT GAG TTT CAT ATG GAA AAT GAT AAA CTT GTT GGG
Asp Cys Gln Leu His Glu Phe His Met Glu Asn Asp Lys Leu Val Gly
                1020
                 *
AAC TTA ACA TGG CGC ATA AAA ACT TTG GAT GGT GGT TTC TTT ACT CGA
Asn Leu Thr Trp Arg Ile Lys Thr Leu Asp Gly Gly Phe Phe Thr Arg
                                                1080
                                                  *
TCT GCT GTG CAA ACA TTT GTT CAA GAT CCA GAT CTT CCT GGA GCA CTT
Ser Ala Val Gln Thr Phe Val Gln Asp Pro Asp Leu Pro Gly Ala Leu
```

FIGURE 1C

```
                                                    1140
                                                     *
TAT AAT CAT GAC AAT GAG TTT CTT CAC TAC CAA GAT GAC TGG TAC ATA
Tyr Asn His Asp Asn Glu Phe Leu His Tyr Gln Asp Asp Trp Tyr Ile

TTA TCT TCC CAA ATC GAA AAC AAA CCC GAT GAT TAC ATA TTC GTA TAC
Leu Ser Gln Ile Glu Asn Lys Pro Asp Asp Tyr Ile Phe Val Tyr
1200
 *
TAC CGA GGT CGA AAC GAC GCA TGG GAT GGA TAC GGT GGG TCC GTG ATC
Tyr Arg Gly Arg Asn Asp Ala Trp Asp Gly Tyr Gly Gly Ser Val Ile
                        1260
                         *
TAC ACC CGA AGC CCG ACA CTC CCC GAA TCG ATC ATC CCA AAC CTA CAA
Tyr Thr Arg Ser Pro Thr Leu Pro Glu Ser Ile Ile Pro Asn Leu Gln

AAA GCA GCC AAA TCC GTG GGT CGA GAC TTT AAC AAT TTC ATA ACA ACC
Lys Ala Ala Lys Ser Val Gly Arg Asp Phe Asn Asn Phe Ile Thr Thr
                                            1380
                                             *
GAC AAT AGT TGT GGG GAG CCT GAG CCT CCA TTG GTG GAA AGG CTT GAG AAA
Asp Asn Ser Cys Gly Glu Pro Glu Pro Pro Leu Val Glu Arg Leu Glu Lys

ACA GCG GAA GAG GGC GAG TTG TTG ATA AAA GAA GCT GTA GAG ATA
Thr Ala Glu Glu Gly Glu Leu Leu Ile Lys Glu Ala Val Glu Ile
```

FIGURE 1D

1440
GAA GAG GTT GAA AAA GAG GTG GAG AAG GTT AGA GAT ACT GAG ATG
Glu Glu Val Glu Lys Glu Val Glu Lys Val Arg Asp Thr Glu Met

1500
ACT TTG TTT CAG AGG TTG CTT GAA GGG TTT AAG GAG TTG CAA CAA GAT
Thr Leu Phe Gln Arg Leu Leu Glu Gly Phe Lys Glu Leu Gln Gln Asp

1560
GAA GAG AAT TTT GTG AGG GAG TTG AGT AAA GAA GAG AAG GAA ATT CTG
Glu Glu Asn Phe Val Arg Glu Leu Ser Lys Glu Glu Lys Glu Ile Leu

1620
AAT GAA CTT CAA ATG GAA GCG ACT GAA GTT GAA AAG CTT TTT GGG CGC
Asn Glu Leu Gln Met Glu Ala Thr Glu Val Glu Lys Leu Phe Gly Arg

1680
GCG TTA CCG ATT AGG AAA CTT AGA TAAATTT CGATGATTGA TTCAGACAAT
Ala Leu Pro Ile Arg Lys Leu Arg

1740
ATATATAGTC ATATGGATTA TGTAGATACT AGAGAAAACC CAAAAAAACT TTTGTATACG

1800
TGATAAACGT GTTTGTGATT TGTTTATTGG CTTAAAATTG TAGAATAGCT TTTTTAATTC

FIGURE 1E

```
                                                                  1860
                                                                    *
TTTACAAAAA AATTGATTGT CTATTGGTAG CCAAGAGGTT CACGAAAAGA CTGAAAGGGT
                                                                  1920
                                                                    *
CTTGCCGGGT TTGCGGGTTA GGCCAAATTT TTTGGGGCGG GATCGGTCTT GATCGGGTTTT
                                                                  1980
                                                                    *
TCTTTAAAAA CATGTATTTT TTATAAATGA TGAGTTATTT TCAATTTTTG GCTAAAAAAAA

```
TATTTTCATG AGTTTGCAGT TGGTGGTAAT ACGGTTGAAG A ATG GCT CTT GCC
CCT                                             M   A   L   A
                                                                P

60
     *
CAT TCA AAT TTT CTG GCC AAC CAT GAA ACC ATC AAA TAT TAT GTT
GGG
 H   S   N   F   L   A   N   H   E   T   I   K   Y   Y   V   G
                120
                 *
TCA AAG CTT CCC GGT CAT AAA AGG TTT AGC TGG GGT TGG GAA GAT
TAC
 S   K   L   P   G   H   K   R   F   S   W   G   W   E   D   Y
                                180
                                 *
TTT GGT AGT ATA GTC GTA GCA AAA ATT TGT TCC AGC AGA CGG ATA
CCT
 F   G   S   I   V   V   A   K   I   C   S   S   R   R   I   P
                                                240
                                                 *
AGA TAC TTT CGA AAA TCT CCT AGA ATA TGC TGT GGT TTG GAT TCA
AGA
 R   Y   F   R   K   S   P   R   I   C   C   G   L   D   S   R

GGT CTG CAA CTA TTC TCA CAC GGG AAA CAC AAT CTC TCT CCC GCA
CAT
 G   L   Q   L   F   S   H   G   K   H   N   L   S   P   A   H
    300
     *
AGC ATT AAC CAG AAT GTA CCT AAG GGA AAT TCA GGA TGC AAA TTT
CCA
 S   I   N   Q   N   V   P   K   G   N   S   G   C   K   F   P
                360
                 *
AAA GAT GTA GCT TTG ATG GTT TGG GAG AAA TGG GGC CAA TTT GCC
AAA
 K   D   V   A   L   M   V   W   E   K   W   G   Q   F   A   K
                                420
                                 *
ACA GCA ATT GTA GCT ATA TTC ATT TTG TCA GTT GCT TCA AAA GCT
GAT
 T   A   I   V   A   I   F   I   L   S   V   A   S   K   A   D
                                                480
                                                 *
GCG GTT GAT GCT CTC AAG ACT TGT ACT TGC TTA CTG AAA GAG TGC
AGG
```

TTA GAG CTT GCG AAG TGC ATT TCG AAC CCT GCA TGT GCA GCT AAT
GTT
 L   E   L   A   K   C   I   S   N   P   A   C   A   A   N   V

540
    *
GCC TGT CTC CAG ACT TGC AAC AAT AGA CCT GAC GAA ACG GAA TGT
CAG
 A   C   L   Q   T   C   N   N   R   P   D   E   T   E   C   Q

600
            *
ATA AAA TGT GGT GAT TTG TTT GAA AAC AGT GTC GTA GAC GAG TTC
AAT
 I   K   C   G   D   L   F   E   N   S   V   V   D   E   F   N

660
                        *
GAG TGT GCA GTC TCC CGA AAG AAA TGT GTA CCT CGT AAA TCT GAT
GTT
 E   C   A   V   S   R   K   K   C   V   P   R   K   S   D   V

720
                                                    *
GGT GAC TTT CCT GTA CCT GAT CCC AGT GTT CTT GTC CAG AAG TTT
GAC
 G   D   F   P   V   P   D   P   S   V   L   V   Q   K   F   D

ATG AAA GAT TTT AGC GGG AAA TGG TTC ATT ACT CGC GGT TTG AAT
CCC
 M   K   D   F   S   G   K   W   F   I   T   R   G   L   N   P

780
    *
ACT TTT GAT GCT TTT GAT TGC CAA TTG CAT GAG TTC CAT ACA GAA
GAA
 T   F   D   A   F   D   C   Q   L   H   E   F   H   T   E   E

840
                *
AAC AAA CTT GTG GGG AAT TTA TCT TGG AGA ATA CGT ACA CCT GAT
GGA
 N   K   L   V   G   N   L   S   W   R   I   R   T   P   D   G

900
                                        *
GGA TTT TTT ACT CGA TCA GCG GTG CAA AAA TTC GTG CAA GAT CCA
AAG
 G   F   F   T   R   S   A   V   Q   K   F   V   Q   D   P   K

```
TAT CCG GGG ATA CTC TAC AAT CAT GAT AAT GAG TAT CTT CTC TAC
CAA
 Y   P   G   I   L   Y   N   H   D   N   E   Y   L   L   Y   Q

GAT GAC TGG TAT ATT TTG TCA TCC AAA GTA GAA AAT AGT CCA GAG
GAT
 D   D   W   Y   I   L   S   S   K   V   E   N   S   P   E   D

1020
  *
TAC ATA TTT GTG TAC TAT AAG GGC AGA AAT GAT GCA TGG GAT GGA
TAT
 Y   I   F   V   Y   Y   K   G   R   N   D   A   W   D   G   Y

1080
                 *
GGT GGT TCT GTA CTT TAC ACA AGA AGT GCA GTT TTG CCT GAA AGC
ATT
 G   G   S   V   L   Y   T   R   S   A   V   L   P   E   S   I

1140
                             *
ATA CCG GAG TTG CAA ACC GCA GCT CAA AAA GTT GGG CGT GAT TTC
AAC
 I   P   E   L   Q   T   A   A   Q   K   V   G   R   D   F   N

1200
                                         *
ACA TTC ATA AAA ACA GAC AAT ACA TGT GGC CCT GAA CCT CCC CTT
GTT
 T   F   I   K   T   D   N   T   C   G   P   E   P   P   L   V

GAG AGG TTG GAG AAG AAA GTG GAA GAA GGA GAA AGG ACG ATC ATA
AAA
 E   R   L   E   K   K   V   E   E   G   E   R   T   I   I   K

1260
  *
GAA GTT GAG GAG ATA GAA GAA GAA GTA GAG AAG GTG AGA GAT AAA
GAA
 E   V   E   E   I   E   E   E   V   E   K   V   R   D   K   E

1320
                   *
GTC ACC TTA TTC AGT AAA CTG TTT GAA GGT TTT AAA GAG CTC CAA
CGA
 V   T   L   F   S   K   L   F   E   G   F   K   E   L   Q   R

1380
                               *
GAT GAA GAG AAC TTC TTA AGA GAG CTG AGC AAA GAA GAA ATG GAT
GTT
 D   E   E   N   F   L   R   E   L   S   K   E   E   M   D   V

```
TTG GAT GGA CTT AAA ATG GAA GCA ACT GAG GTA GAA AAA CTT TTT
                                              *
GGG
 L   D   G   L   K   M   E   A   T   E   V   E   K   L   F   G

1500
*
CGT GCT TTA CCA ATA AGG AAA TTA A GGTAAGT ATTTTTAAAA
CTATCAACAT
 R   A   L   P   I   R   K   L   X

1560
*
ATATACTACA TGTATAGTTG TATTTGATTC TTTTGCCTGG AATAGATTGC

TTATACATCA TGTATTGCTT CTTTTTCAGA AGCAAAAAA
```

FIGURE 2D

```
CCACGCGTCC GGCTTGGTGT GGGGAAGATT AGATAGTGTG A AGA ATG GCA GTA GCT
                                              R   M   A   V   A
   60
    *
ACA CAT TGT TTC ACT TCA CCT TGT CAT GAC CGT ATT CGA TTT TTC TCA
 T   H   C   F   T   S   P   C   H   D   R   I   R   F   F   S
            120
             *
AGT GAT GAT GGT ATT GGT AGG CTT GGC ATT ACA AGA AAG AGG ATC AAT
 S   D   D   G   I   G   R   L   G   I   T   R   K   R   I   N
                        180
                         *
GGC ACT TTC TTG CTC AAG ATT TTA CCT CCA ATC CAA AGT GCT GAT CTC
 G   T   F   L   L   K   I   L   P   P   I   Q   S   A   D   L
                                                240
                                                 *
AGA ACA ACT GGT GGG AGA TCC TCA CGT CCT TTA TCT GCA TTC AGG TCA
 R   T   T   G   G   R   S   S   R   P   L   S   A   F   R   S

GGA TTC TCT AAG GGG ATA TTT GAC ATT GTG CCA TTA CCA TCA AAG AAT
 G   F   S   K   G   I   F   D   I   V   P   L   P   S   K   N
   300
    *
GAG CTG AAA GAG CTG ACC GCT CCG CTG TTG CTA AAA CTC GTG GGT GTT
 E   L   K   E   L   T   A   P   L   L   L   K   L   V   G   V
                        360
                         *
TTA GCT TGC GCG TTC CTT ATT GTT CCA TCT GCA GAT GCA GTT GAT GCA
 L   A   C   A   F   L   I   V   P   S   A   D   A   V   D   A
                                    420
                                     *
CTT AAA ACT TGT GCA TGC TTA TTG AAG GGA TGC AGG ATA GAA CTC GCA
 L   K   T   C   A   C   L   L   K   G   C   R   I   E   L   A
                                                    480
                                                     *
AAG TGC ATT GCC AAC CCT GCC TGT GCA GCC AAT GTC GCG TGC CTT CAG
 K   C   I   A   N   P   A   C   A   A   N   V   A   C   L   Q

ACC TGC AAT AAC CGT CCA GAT GAA ACC GAG TGC CAG ATT AAA TGT GGG
 T   C   N   N   R   P   D   E   T   E   C   Q   I   K   C   G
   540
    *
GAT CTG TTT GAG AAC AGT GTT GTT GAT GAG TTC AAC GAG TGT GCT GTG
 D   L   F   E   N   S   V   V   D   E   F   N   E   C   A   V

```
TCG AGA AAA AAG TGT GTT CCT AGA AAA TCT GAT CTC GGA GAA TTT CCT
 S   R   K   K   C   V   P   R   K   S   D   L   G   E   F   P
                                        660
GCC CCA GAC CCT TCT GTT CTT GTA CAG AAC TTC AAC ATC TCG GAC TTT
 A   P   D   P   S   V   L   V   Q   N   F   N   I   S   D   F
                                                    720
AAC GGG AAG TGG TAC ATT ACA AGT GGC TTG AAT CCA ACC TTT GAT GCC
 N   G   K   W   Y   I   T   S   G   L   N   P   T   F   D   A

TTC GAC TGC CAG CTG CAT GAG TTC CAC ACA GAA GGT GAC AAC AAG CTT
 F   D   C   Q   L   H   E   F   H   T   E   G   D   N   K   L
     780
GTT GGA AAC ATC TCT TGG AGA ATA AAG ACC CTA GAC AGT GGA TTC TTT
 V   G   N   I   S   W   R   I   K   T   L   D   S   G   F   F
                   840
ACT AGG TCA GCC GTA CAA AAA TTC GTG CAA GAT CCT AAC CAA CCT GGT
 T   R   S   A   V   Q   K   F   V   Q   D   P   N   Q   P   G
                                        900
GTT CTC TAC AAT CAT GAC AAC GAG TAC CTT CAC TAT CAA GAT GAC TGG
 V   L   Y   N   H   D   N   E   Y   L   H   Y   Q   D   D   W
                                                    960
TAT ATC CTG TCA TCA AAG ATA GAG AAT AAA CCT GAA GAC TAT ATA TTT
 Y   I   L   S   S   K   I   E   N   K   P   E   D   Y   I   F

GTA TAC TAC CGT GGG CGA AAC GAT GCT TGG GAT GGA TAT GGT GGT GCA
 V   Y   Y   R   G   R   N   D   A   W   D   G   Y   G   G   A
     1020
GTT GTA TAC ACG AGA AGT TCT GTA TTA CCC AAT AGC ATT ATA CCA GAA
 V   V   Y   T   R   S   S   V   L   P   N   S   I   I   P   E
                   1080
CTC GAA AAA GCA GCA AAA AGC ATA GGC AGA GAC TTC AGC ACA TTC ATT
 L   E   K   A   A   K   S   I   G   R   D   F   S   T   F   I
                                        1140
AGA ACG GAT AAC ACA TGT GGT CCT GAA CCT GCG CTC GTG GAG AGA ATT
 R   T   D   N   T   C   G   P   E   P   A   L   V   E   R   I
```

FIGURE 3B

```
                                                          1200
                                                            *
GAG AAG ACA GTG GAA GAA GGT GAA AGG ATA ATC GTA AAA GAG GTT GAA
 E   K   T   V   E   E   G   E   R   I   I   V   K   E   V   E

GAG ATA GAA GAA GAG GTA GAG AAG GAA GTG GAG AAG GTC GGT AGG ACT
 E   I   E   E   E   V   E   K   E   V   E   K   V   G   R   T
1260
  *
GAG ATG ACC TTG TTC CAG AGA TTG GCT GAA GGA TTT AAT GAA CTG AAG
 E   M   T   L   F   Q   R   L   A   E   G   F   N   E   L   K
                1320
                  *
CAA GAC GAG GAG AAT TTC GTG AGA GAG TTA AGT AAA GAA GAG ATG GAG
 Q   D   E   E   N   F   V   R   E   L   S   K   E   E   M   E
                                1380
                                  *
TTT TTG GAT GAG ATC AAA ATG GAA GCA AGT GAG GTT GAA AAA TTG TTT
 F   L   D   E   I   K   M   E   A   S   E   V   E   K   L   F
                                                1440
                                                  *
GGG AAA GCT TTG CCA ATC AGG AAG GTC A GG TAGAAACAAG AACCACCATT
 G   K   A   L   P   I   R   K   V   X
                                                          1500
                                                            *
GTTGTACAAA CTATATTATA CATACTGTGT TCGGTTCATA TAAAGTAATA TTTTTGTACA

CAGTCATCAT CATTCCATAA CAATTGGATA AAAAAAAAAA AAAAA
```

FIGURE 3C

```
Tobacco      MALAPHSNFLANHETIKYYVGSKLPGHKRFSWGWEDYFGSIVVAKICSSR    50
Arabidopsis  M-V-T-............CFT-PCHDRI--FSS.D-GI-RLGITRK....    33
Lettuce      M--SL-TV--CKE-ALNL-AR-PCNE..--HRS.GQPPTN-IMM--....    43

Tobacco      RIPRYFRKSPRICCGLDSRGLQLF.SHGKHNLSPAHSINQNVPKGNSGCK    99
Arabidopsis  --NGT-L..LK-LPPIQ-AD-RTTGGRSSRP--AFR-GFSKGIFDIVPLP    81
Lettuce      -SNNGYFN-F-LFTSYKTSSF..SD-SHCKDK-QI.CSIDTSFEEIQRFD    90

Tobacco      FPKDVALMVWEKWGQFAKTAIVAIFILSVASKADA                   134
Arabidopsis  SKNELKELTA...PLLL-LVG-LACAFLIVPS---                   113
Lettuce      LKRGMT-ILEKQ-R--IQL---LVCTFVIVPRV--                   125

* *   *      *      *    * *          *   *
Tobacco      VDALKTCTCLLKECRLELAKCISNPACAANVACLQTCNNRPDETECQIKC    50
Arabidopsis  -------A----G--I------A---------------------------   50
Lettuce      -------A--------I------A--S-----------------------   50
                     *  *
Tobacco      GDLFENSVVDEFNECAVSRKKCVPRKSDVGDFPVPDPSVLVQKFDMKDFS   100
Arabidopsis  ---------------------------L-E--A---------N-NIS--N   100
Lettuce      ---------Q-----------------E-----RNAV--N-N-------   100
                                  *
Tobacco      GKWFITRGLNPTFDAFDCQLHEFHTE.ENKLVGNLSWRIRTPDGGFFTRS   149
Arabidopsis  ---Y--S-----------------GD------I----K-L-S------    150
Lettuce      ---Y--S----------------M-ND.------T---K-L--------   149

Tobacco      AVQKFVQDPKYPGILYNHDNEYLLYQDDWYILSSKVENSPEDYIFVYYKG   199
Arabidopsis  ---------NQ--V--------H------------I--K---------R-   200
Lettuce      ---T-----DL--A-------F-H---------QI--K-D-------R-   199
                                                    *
Tobacco      RNDAWDGYGGSVLYTRSAVLPESIIPELQTAAQKVGRDFNTFIKTDNTCG   249
Arabidopsis  -----------A-V----S---N------EK--KSI----S---R-----   250
Lettuce      ------------I---PT-------N--K--KS------N--T---S--   249

Tobacco      PEPPLVERLEKKVEEGERTIIKEVEEIEE....EVEKVRDKEVTLFSKLF   295
Arabidopsis  ---A----I--T------I-V--------EVEK-----GRT-M---QR-A   300
Lettuce      ------------TA----KLL---AV----EVEK-------T-M---QR-L  299

Tobacco      EGFKELQRDEENFLRELSKEEMDVLDGLKMEATEVEKLFGRALPIRKLR    344
Arabidopsis  ---N--KQ-----V--------EF--EI----S-------K------V-   349
Lettuce      -------Q-----V-------KEI-NE-Q--------------------   348
```

FIGURE 4B

Percent Identity and Similarity* of Pre-protein VDE

|  | Lettuce | Tobacco | Arabidopsis |
|---|---|---|---|
| Lettuce |  | 67 (78) | 69 (82) |
| Tobacco | 69 |  | 68 (81) |
| Arabidopsis | 66 | 68 |  |

*protein / cDNA*

*similarity values are in parentheses

Percent Identity and Similarity* of Mature VDE

|  | Lettuce | Tobacco | Arabidopsis |
|---|---|---|---|
| Lettuce |  | 82 (90) | 83 (91) |
| Tobacco | 76 |  | 83 (92) |
| Arabidopsis | 74 | 77 |  |

*protein / cDNA*

*similarity values are in parentheses

FIGURE 5

| Plant | Treatment | N | V | A | Z | V+A+Z | L | Chlb/Chla | ßß-Carotene | %V Deepoxidized |
|---|---|---|---|---|---|---|---|---|---|---|
| Ct-11 | Dark | 77.13 | 64.67 | 1.54 | 0 | 66.21 | 335.12 | 0.39 | 136.95 | |
| | Light | 77.65 | 25.56 | 6.25 | 30.93 | 62.74 | 338.15 | 0.40 | 131.76 | 60.5 |
| Ct-14 | Dark | 71.60 | 77.74 | 1.19 | 0 | 78.93 | 312.05 | 0.36 | 150.08 | |
| | Light | 72.00 | 29.07 | 7.97 | 43.07 | 80.11 | 311.36 | 0.37 | 151.50 | 62.6 |
| Ct-15 | Dark | 76.68 | 67.44 | 0 | 0 | 67.44 | 345.73 | 0.43 | 130.05 | |
| | Light | 74.45 | 26.73 | 7.78 | 37.44 | 71.95 | 337.87 | 0.42 | 126.36 | 60.4 |
| Ct-18 | Dark | 68.28 | 82.55 | 2.33 | 0 | 84.88 | 298.36 | 0.35 | 136.67 | |
| | Light | 69.65 | 34.50 | 13.25 | 38.44 | 86.19 | 311.07 | 0.36 | 138.95 | 58.2 |
| Ct-20 | Dark | 78.45 | 70.60 | 2.85 | 0 | 73.45 | 351.57 | 0.39 | 139.58 | |
| | Light | 77.38 | 23.14 | 5.46 | 42.66 | 71.26 | 343.25 | 0.39 | 133.61 | 67.2 |
| Ct-22 | Dark | 72.68 | 104.14 | 3.40 | 0 | 107.54 | 323.93 | 0.37 | 138.29 | |
| | Light | 72.13 | 27.63 | 6.62 | 78.66 | 112.91 | 315.07 | 0.40 | 128.30 | 73.5 |
| Ct-24 | Dark | 70.77 | 76.82 | 1.55 | 0 | 78.37 | 334.20 | 0.43 | 132.95 | |
| | Light | 76.52 | 29.35 | 7.92 | 45.24 | 82.51 | 339.60 | 0.44 | 131.55 | 61.8 |
| Ct-26 | Dark | 75.28 | 63.41 | 0 | 0 | 63.41 | 346.45 | 0.44 | 130.38 | |
| | Light | 77.34 | 26.27 | 6.16 | 34.19 | 66.62 | 346.91 | 0.44 | 128.27 | 58.6 |
| Ct-30 | Dark | 78.23 | 59.66 | 1.73 | 0 | 61.39 | 357.63 | 0.45 | 127.62 | |
| | Light | 79.37 | 26.47 | 4.93 | 31.81 | 63.01 | 352.39 | 0.46 | 124.80 | 55.6 |
| Ct-31 | Dark | 71.72 | 75.91 | 1.74 | 0 | 77.65 | 315.40 | 0.37 | 144.24 | |
| | Light | 73.00 | 31.43 | 8.74 | 37.65 | 77.82 | 312.80 | 0.38 | 145.13 | 58.6 |
| Ct-39 | Dark | 75.99 | 77.93 | 1.73 | 0 | 77.93 | 335.79 | 0.43 | 127.17 | |
| | Light | 74.79 | 26.28 | 8.07 | 41.30 | 75.65 | 331.35 | 0.42 | 123.11 | 66.3 |
| Ct-40 | Dark | 77.56 | 79.07 | 2.99 | 0 | 82.06 | 358.33 | 0.44 | 126.05 | |
| | Light | 77.78 | 27.44 | 10.10 | 47.92 | 85.46 | 352.66 | 0.43 | 120.89 | 65.3 |

Mean = 62.4 ± 5.0

N = 9'-cis-neoxanthin  V = violaxanthin  A = antheraxanthin  Z = zeaxanthin  L = lutein  Chla = chlorophyll $a$  Chlb = chlorophyll $b$
All values are relative to chlorophyll $a$ (mmol mol$^{-1}$ Chla) except Chlb/Chla which is (mol/mol).

FIGURE 8A

| Plant | Treatment | N | V | A | Z | V+A+Z | L | Chlb/Chla | Bß-Carotene | %V De-epoxidized | % Inhibition of De-epoxidation |
|---|---|---|---|---|---|---|---|---|---|---|---|
| TAS-32 | Dark | 74.19 | 76.98 | 0 | 0 | 76.98 | 325.75 | 0.42 | 136.45 | | |
|  | Light | 73.78 | 74.15 | 2.18 | 0 | 76.33 | 330.95 | 0.41 | 131.73 | 3.7 | 94.1 |
| TAS-39 | Dark | 77.92 | 59.19 | 0 | 0 | 59.19 | 329.29 | 0.41 | 141.45 | | |
|  | Light | 75.06 | 56.39 | 2.70 | 0 | 59.09 | 322.29 | 0.40 | 141.52 | 4.7 | 92.5 |
| TAS-21 | Dark | 75.78 | 53.19 | 0 | 0 | 53.19 | 335.21 | 0.45 | 132.85 | | |
|  | Light | 77.92 | 43.90 | 7.30 | 9.37 | 60.57 | 326.90 | 0.45 | 130.33 | 17.5 | 72.0 |
| TAS-5 | Dark | 67.82 | 79.21 | 3.43 | 0 | 82.64 | 300.82 | 0.39 | 139.00 | | |
|  | Light | 69.72 | 62.31 | 14.66 | 8.27 | 85.24 | 300.63 | 0.40 | 137.13 | 21.3 | 65.9 |
| TAS-17 | Dark | 74.89 | 64.54 | 1.08 | 0 | 65.62 | 317.69 | 0.41 | 143.42 | | |
|  | Light | 74.00 | 49.89 | 8.49 | 8.53 | 66.91 | 325.32 | 0.40 | 139.28 | 22.7 | 63.6 |
| TAS-13 | Dark | 77.92 | 49.33 | 1.27 | 0 | 50.60 | 339.63 | 0.45 | 135.36 | | |
|  | Light | 78.02 | 37.82 | 4.94 | 7.18 | 49.94 | 340.45 | 0.45 | 132.78 | 23.3 | 62.7 |
| TAS-6 | Dark | 74.42 | 55.77 | 0 | 0 | 55.77 | 340.84 | 0.44 | 136.77 | | |
|  | Light | 74.95 | 40.27 | 9.69 | 13.99 | 63.95 | 332.00 | 0.44 | 135.36 | 27.8 | 55.4 |
| TAS-37 | Dark | 73.05 | 59.18 | 1.24 | 0 | 60.42 | 323.30 | 0.39 | 135.81 | | |
|  | Light | 71.36 | 38.97 | 14.48 | 9.98 | 63.43 | 313.46 | 0.38 | 134.62 | 34.1 | 45.3 |
| TAS-3 | Dark | 74.04 | 60.25 | 1.76 | 0 | 62.01 | 319.39 | 0.43 | 138.89 | | |
|  | Light | 76.98 | 39.26 | 7.41 | 14.33 | 61.00 | 322.14 | 0.44 | 136.00 | 34.8 | 44.2 |
| TAS-36 | Dark | 69.77 | 77.88 | 1.42 | 0 | 79.28 | 295.52 | 0.36 | 151.33 | | |
|  | Light | 70.74 | 48.73 | 12.76 | 12.81 | 74.30 | 308.06 | 0.36 | 151.35 | 37.4 | 40.1 |
| TAS-35 | Dark | 75.59 | 63.24 | 1.05 | 0 | 64.29 | 342.09 | 0.42 | 130.30 | | |
|  | Light | 75.76 | 39.48 | 10.38 | 17.49 | 67.35 | 337.57 | 0.42 | 126.88 | 37.6 | 39.7 |
| TAS-4 | Dark | 73.61 | 68.23 | 1.31 | 0 | 69.54 | 321.12 | 0.42 | 135.43 | | |
|  | Light | 73.23 | 42.07 | 8.95 | 17.84 | 68.86 | 320.33 | 0.42 | 131.73 | 38.3 | 38.6 |
| TAS-9 | Dark | 72.28 | 52.57 | 1.75 | 0 | 54.32 | 324.02 | 0.42 | 140.21 | | |
|  | Light | 73.28 | 31.72 | 6.19 | 18.59 | 56.50 | 317.11 | 0.42 | 136.93 | 39.7 | 36.4 |
| TAS-7 | Dark | 72.55 | 71.02 | 1.81 | 0 | 72.83 | 321.37 | 0.40 | 133.21 | | |

FIGURE 8B

|  | | Light/Dark | | | | | | | | |
|---|---|---|---|---|---|---|---|---|---|---|
|  |  | N | V | A | Z | L | Chla | Chlb | Chla+b | Chlb/Chla |
| TAS-38 | Light | 71.79 | 39.82 | 14.04 | 21.09 | 74.95 | 322.04 | 0.40 | 130.57 | 29.6 |
|  | Dark | 71.66 | 61.97 | 1.77 | 0 | 63.74 | 329.67 | 0.41 | 135.87 | 28.8 |
|  | Light | 73.24 | 34.45 | 8.83 | 19.57 | 62.85 | 331.17 | 0.41 | 133.77 |  |
| TAS-16 | Dark | 72.15 | 62.54 | 2.04 | 0 | 64.58 | 329.72 | 0.41 | 135.12 | 25.0 |
|  | Light | 74.04 | 33.28 | 9.10 | 23.83 | 66.21 | 335.60 | 0.42 | 131.32 |  |
| TAS-18 | Dark | 75.09 | 59.64 | 1.72 | 0 | 61.36 | 345.04 | 0.42 | 127.38 | 24.8 |
|  | Light | 75.26 | 31.68 | 7.11 | 23.01 | 61.80 | 340.79 | 0.42 | 126.85 |  |
| TAS-34 | Dark | 72.35 | 65.39 | 1.79 | 0 | 67.18 | 326.06 | 0.41 | 131.12 | 23.7 |
|  | Light | 71.25 | 34.26 | 9.26 | 30.41 | 73.93 | 316.49 | 0.42 | 128.96 |  |

N = 9'-cis-neoxanthin  V = violaxanthin  A = antheraxanthin  Z = zeaxanthin  L = lutein  Chla = chlorophyll a  Chlb = chlorophyll b All values are relative to chlorophyll a (mmol mol-1 Chla) except Chlb/Chla which is (mol/mol).

|  | Dark-adapted | Pre-illuminated | Post-fluorescence Analysis |
|---|---|---|---|
| V | 64.28 | 51.77 | 44.98 |
| A | 1.99 | 6.16 | 11.10 |
| Z | 0 | 10.17 | 13.77 |
| V+A+Z | 66.27 | 68.10 | 69.85 |
| De-epoxidation (%) |  | 19.5 | 30.00 |
| (Fm/Fm') - 1 |  |  | 2.20 |
| (Fo/Fo') - 1 |  |  | 0.15 |

All values are relative to chlorophyll a (mmol mol$^{-1}$ Chla).

TAS-5

|  | Dark-adapted | Pre-illuminated | Post-fluorescence Analysis |
|---|---|---|---|
| V | 67.51 | NA | 65.38 |
| A | 0 | NA | 2.14 |
| Z | 0 | NA | 0 |
| V+A+Z | 67.51 | NA | 67.52 |
| De-epoxidation (%) |  | NA | 3.20 |
| (Fm/Fm') - 1 |  |  | 1.34 |
| (Fo/Fo') - 1 |  |  | 0 |

All values are relative to chlorophyll a (mmol mol$^{-1}$ Chla).
NA - Not assayed

PLANT VDE GENES AND METHODS RELATED THERETO

This Application is a continuation in part of U.S. application Ser. No. 08/747,574 filed Nov. 7, 1996 now U.S. Pat. No. 6,015,939 issued Jan. 18, 2000 which claims benefit of U.S. Provisional Application 60/006,315 filed Nov. 7, 1995 and U.S. Provisional Application 60/023,502 filed Aug. 6, 1996.

FIELD OF THE INVENTION

This invention relates to genes encoding plant violaxanthin de-epoxidase (vde) and methods of use related to the protein and the nucleic acid sequences. The invention is exemplified by methods of causing increased expression or decreased expression of plant vde genes in plants. Included are plants produced by the method.

INTRODUCTION

Background

Plant carotenoids are found in the membranes of chloroplasts and chromoplasts. They are instrumental in the photoprotective mechanisms of plants. Also, plant carotenoids have significant dietary implications. Thus, from an agronomic as well as a nutritional standpoint, study of the plant carotenoids and the enzymes involved in the biosynthesis of carotenoids is of interest.

Of particular interest are the late stages of the carotenoid biosynthetic pathway in plants, the xanthophyll cycle and its importance in photoregulation of photosynthesis. Photosynthesis is the process that enable plants to use light energy for growth and development. Thus, the availability of light of appropriate quality and quantity (photosynthetically active radiation or "PAR") is critical for plant growth and development. Ironically, light can also damage plants because plants have limited capacity to use light. When light intensity exceeds this capacity, irreversible damage can occur.

Plants have developed various mechanisms to cope with excess light such as varying leaf orientation or developing reflective surfaces. Such mechanisms appear to be specialized phenotypic strategies that are limited to certain types of plants. One mechanism that is apparently used by all plants examined so far is the dissipation of excess energy as heat in the antenna (light absorbing structures) of the photosynthetic apparatus. Most of the excess energy is discarded as heat by a complex feed-back regulatory system that involves the transthylakoid ApH and formation of antheraxanthin and zeaxanthin catalyzed by violaxanthin de-epoxidase (vde) in the xanthophyll cycle. This system, termed energy dependent non-radiative energy dissipation or non-photochemical fluorescence quenching, reduces the quantum efficiency of photosystem II (PSII), helping to prevent PSII over reduction and photoinhibitory damage. In effect, this system provides a means to dump excess energy before it can damage the photosynthetic apparatus. The system has a wide dynamic range, both qualitatively and quantitatively, which enables it to function effectively over a wide-range of environmental conditions.

The ability to manipulate aspects of the xanthophyll cycle through genetic engineering techniques would permit the rapid introduction of improved plant varieties. However, it has been difficult to obtain purified fractions of the enzymes involved in the pathway and, prior to this invention, the corresponding genes have not been cloned.

SUMMARY OF THE INVENTION

DNA sequences encoding plant vde enzymes are provided herein. The sequences may be joined to heterologous DNA sequences for use as probes and in DNA constructs to modify the genotype of a host organism. DNA constructs and methods are provided to modify a host cell phenotype by altering the amount of photoprotection enzyme present in the host cell. In plastid containing host cells, zeaxanthin levels and sensitivity to light can be modified through alterations in the level of vde enzymes.

For example, over expression of vde is expected to increase the tolerance of plants to high light, drought and temperature stress (stress conditions exacerbate the condition of excess light). Also, plants that are not currently tolerant to high light or low temperatures are expected to become more tolerant to these stresses. Plants that are better adapted to light stress are expected to be more productive and/or more resistant to disease. Alternatively, the under expression, or inhibition of vde activity is expected to increase photosynthetic efficiency under low light. The growing range of plants, crops, trees and ornamentals, could thus be modified.

Specific plant vde's are described. In particular, a 55 kD lettuce vde having the cDNA sequence and deduced amino acid sequence as shown in FIG. 1, a tobacco vde having the cDNA sequence and deduced amino acid sequence as shown in FIG. 2, and an *Arabidopsis* vde having the cDNA sequence and deduced amino acid sequence as shown in FIG. 3, are described. FIG. 4 provides a comparison at the amino acid level of the proteins of FIGS. 1–3. In this amino acid sequence comparison the trasit peptides for the three sequences are boxed. Identical amino acids are denoted by a hyphen. Gaps inserted to optimize sequence alignments are denoted with a period. The thirteen highly conserved cysteine residues are denoted with an asterisk.

FIG. 5 is a comparison of the identity and similarity of pre-protein and mature protein vde. As can be seen from FIG. 5, diverse vde's have sequences with about 75% sequence identity with one another at the amino acid level. Thus, vde sequences having at least about 75% homology to amino acid sequences in FIG. 1, FIG. 2 or FIG. 3 are also contemplated hereunder.

Nucleic acid sequences encoding a plant vde having at least about 60% sequence identity, and more preferably at least about 70% sequence identity, with the sequences in FIG. 1, 2 or 3, and are likewise contemplated herein. For instance, a comparison of tobacco and lettuce vde nucleic acid sequences give 76% identity, excluding the transit peptides. A high degree of sequence identity at the N-terminus is particularly preferred. Other related plant photoregulatory sequences having high degrees of similarity with fragments of the vde sequences shown are also contemplated.

In a different aspect of this invention, nucleic acid sequences related to the exemplified lettuce, tobacco and *arabidopsis* vde sequences of this invention are described with details regarding methods to obtain such sequences from a variety of sources and their use. In addition, cDNA sequences encoding mature vde's are given as well as transit peptides, mRNA, genomic plant vdes, and plant vde regulatory regions.

In a further aspect of this invention, methods of producing vde in host cells are described. In plastid containing cells, modifications in the xanthophyll cycle, particularly in the ratio of violaxanthin as to zeaxanthin are contemplated via increased production of vde or decreased production of vde. This will have applications in the increased feed value of plants. Zeaxanthin levels are important to crops such as alfalfa whose value in part is due to xanthophyll content.

Results from studies of transgenic plants demonstrates that xanthophyll-mediated energy dissipation in LHCII apparently protects PSII against the potentially damaging effects of high light. This protection is induced by the combined effects of a thylakoid ΔpH and the presence of zeaxanthin and antheraxanthin formed by violaxanthin de-epoxidase (vde) activity.

DESCRIPTION OF THE FIGURES

FIGS. 1A, 1B, 1C, 1D, 1E and 1F provide the cDNA sequence (SEQ ID NO:1 and 2) for romaine lettuce vde and deduced polypeptide sequence. The underlined sequences are those determined from peptide sequencing of purified lettuce vde. The polypeptide sequence begins at the first methionine of the open reading frame and is preceded by three termination codons in the same reading frame.

FIGS. 2A, 2B, 2C and 2D provide the cDNA sequence (SEQ ID NO:3 and 4) for tobacco (*Nicotiana tabacum* cv. Xanthi) vde and deduced polypeptide sequence.

FIGS. 3A, 3B and 3C provide the cDNA sequence (SEQ ID NO:5 and 6) for *Arabidopsis thaliana* (var. *Columbia*) vde and deduced polypeptide sequence.

FIG. 4B provides a comparison of the amino acid sequences (SEQ ID NO:2, 4 and 6) of the proteins of FIGS. 1–3.

FIG. 5 shows the percent similarity between the proteins of FIGS. 1–3.

FIGS. 8A, 8B and 8C are tables.

DETAILED DESCRIPTION OF THE INVENTION

Figure 4A:
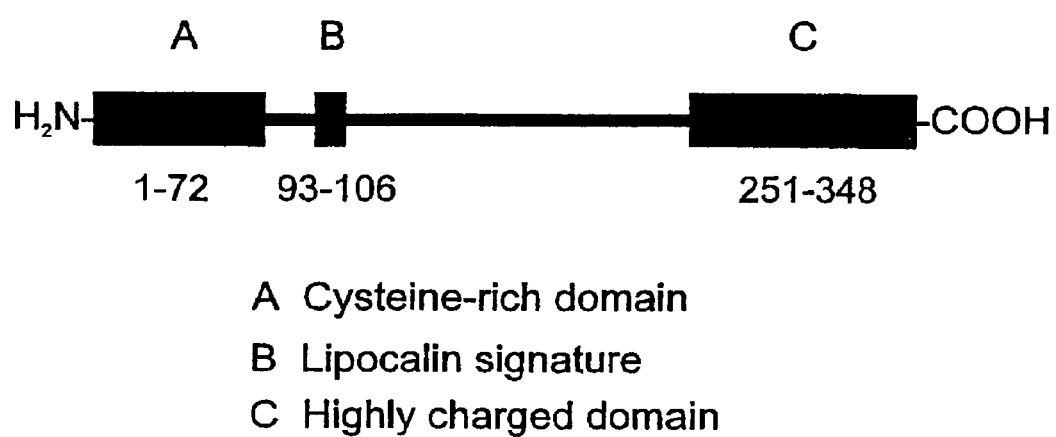
FIG. 4A provides, a map showing the location of three domains in the deduced protein.

A plant violaxanthin de-epoxidase or "vde" of this invention includes any sequence of amino acids, such as a protein, polypeptide or peptide, obtainable from a plant source, which demonstrates the ability to catalyze the production of zeaxanthin from violaxanthin under plant enzyme reactive conditions. By "enzyme reactive conditions" is meant that any necessary conditions that are available in an environment (i.e., such factors as temperature, pH, lack of inhibiting substances) which will permit the enzyme to function.

By "plant" is meant any plastid-containing organism. A "higher plant" shall mean any differentiated, multi-cellular plastid-containing organism. Of particular interest are plant vde's from angiosperms, both dicotyledonous and monocotyledonous plants.

In this invention, the cDNA sequence of a lettuce (FIG. 1), tobacco (FIG. 2) and *Arabidopsis* (FIG. 3) vde gene are provided. Transit peptide regions are identified in FIG. 4. From these sequences, genomic sequences may be obtained and the corresponding transcriptional and translational regulatory regions determined. Also, using the lettuce and/or tobacco sequences provided, vde genes from other sources may be obtained. In particular, it is found that the N-terminal regions of the lettuce, tobacco, *Arabidopsis* and spinach proteins are conserved and her ore, an N-terminal peptide such as "VDALKTCACLLK" (SEQ ID no:7) will find particular use in obtaining related sequences.

Constructs for use in the methods may include several forms, depending upon the intended use of the construct. Thus, the constructs include vectors, transcriptional cassettes, expression cassettes and plasmids. The transcriptional and translational initiation region (also sometimes referred to as a "promoter") preferably comprises a transcriptional initiation regulatory region and a translational initiation regulatory region of untranslated 5' sequences, "ribosome" binding sites," responsible for binding mRNA to ribosomes and translational initiation. It is preferred that all of the transcriptional and translational functional elements of the initiation control region are derived from or obtainable from the same gene. In some embodiments, the promoter will be modified by the addition of sequences, such as enhancers, or deletions of nonessential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

A transcriptional cassette for transcription of a nucleotide sequence of interest will include in the direction of transcription, a transcription initiation region and, optionally a translational initiation region, a DNA sequence of interest, and a transcriptional and optionally translational termination region functional in the host cell of interest. When the cassette provides for the transcription and translation of a DNA sequence it is considered an expression cassette. One or more introns may also be present. Other sequences may also be present, including those encoding transit peptides.

The use of amino acid sequences from vde peptides to obtain nucleic acid sequences which encode lettuce vde is described herein. For example, synthetic oligonucleotides are prepared which correspond to the vde peptide sequences. The oligonucleotides are used as primers in polymerase chain reaction (PCR) techniques to obtain partial DNA sequence of vde genes. The partial sequences so obtained are then used as probes to obtain vde clones from a gene library prepared from lettuce tissue. Alternatively, where oligonucleotides of low degeneracy can be prepared from particular vde peptides, such probes may be used directly to screen gene libraries for vde gene sequences. In particular, screening of cDNA libraries in phage vectors is useful in such methods due to lower levels of background hybridization.

A nucleic acid sequence of a plant vde of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the vde protein) may be synthesized using codons preferred by a selected host. Host-preferred codons may be determined, for example, from the codons used most frequently in the proteins expressed in a desired host species.

One skilled in the art will readily recognize that antibody preparations, nucleic acid probes (DNA and RNA) and the like may be prepared and used to screen and recover "homologous" or "related" vde's from a variety of plant sources. Homologous sequences are found when there is an identity of sequence, which may be determined upon comparison of sequence information, nucleic acid or amino acid, or through hybridization reactions between a known vde and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature proteins. (See generally, Doolittle, R. F., *OF URFS and ORFS* (University Science Books, CA, 1986.)

Thus, other plant vde's may be obtained from the specific exemplified lettuce, tobacco and *Arabidopsis* sequences provided herein. Furthermore, it will be apparent that one can obtain natural and synthetic plant vde's, including modified amino acid sequences and starting materials for synthetic-protein modeling from the exemplified plant vde's and from plant vde's which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

Typically, a plant vde sequence obtainable from the use of nucleic acid probes will show 60–70% sequence identity between the target vde sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding a vde enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related vde genes. Shorter probes are often particularly useful for polymerase chain reactions (PCR), especially when highly conserved sequences can be identified. (See, Gould, et al., *PNAS USA* (1989) 86:1934–1938.)

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285).

A useful probe and appropriate hybridization and washing conditions having been identified as described above; cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences. When a genomic library is used, one or more sequences may be identified providing both the coding region and the transcriptional regulatory elements of the vde gene from such plant source.

For immunological screening, antibodies to the vde protein can be prepared by injecting rabbits or mice with the protein purified from the original plant source or expressed from a host cell, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the vde. When cross-reactivity is observed, genes encoding the related proteins are isolated by screening expression libraries representing the desired plant species. Expression libraries can be constructed in a variety of commercially available vectors, including lambda gtll, as described in Maniatis, et al. (supra).

All plants studied to date utilize the xanthophyll cycle, and thus any given plant species can be considered as a source of additional vde proteins.

The nucleic acid sequences associated with plant vde proteins will find many uses. For example, recombinant constructs can be prepared which can be used as probes or will provide for expression of the vde protein in host cells to produce a ready source of the enzyme. Other useful applications may be found when the host cell is a plant host cell, either in vitro or in vivo. For example, by increasing the amount of a respective vde available to the plant xanthophyll cycle, an increased percentage of zeaxanthin may be obtained. In a like manner, for some applications it may be desired to decrease the amount of vde endogenously expressed in a plant cell by anti-sense or some other reducing technology such as co-supression. For example, to improve photosynthetic efficiency of a plant under low light, decreased expression of a vde may be desired.

Thus, depending upon the intended use, the constructs may contain the sequence which encodes the entire vde protein, or a portion thereof. For example, where antisense inhibition of a given vde protein is desired, the entire vde sequence is not required. Furthermore, where vde constructs are intended for use as probes, it may be advantageous to prepare constructs containing only a particular portion of an vde encoding sequence, for example a sequence which is discovered to encode a highly conserved vde region.

As discussed above, nucleic acid sequence encoding a plant vde of this invention may include genomic, cDNA or mRNA sequence. By encoding is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

A cDNA sequence may or may not contain pre-processing sequences, such as transit peptide sequences or targeting sequences to facilitate delivery of the vde protein to a given organelle or membrane location. The use of such precursor vde DNA sequences is preferred for uses in plant cell expression. A genomic vde sequence may contain the transcription and translation initiation regions, introns, and/or transcript termination regions of the plant vde, which sequences may be used in a variety of DNA constructs, with or without the vde structural gene. Thus, nucleic acid sequences corresponding to the plant vde of this invention may also provide signal sequences useful to direct protein delivery into a particular organelle or membrane location, 5' upstream non-coding regulatory regions (promoters) having useful tissue and timing profiles, 3' downstream non-coding regulatory region useful as transcriptional and translational regulatory regions and may lend insight into other features of the gene.

Once the desired plant vde nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant vde of this invention may be combined with other non-native, or "heterologous", sequences in a variety of ways. By "heterologous" sequences is meant any sequence which is not naturally found joined to the plant vde, including, for example, combinations of nucleic acid sequences from the same plant which are not naturally found joined together.

The DNA sequence encoding a plant vde of this invention may be employed in conjunction with all or part of the gene sequences normally associated with the vde. In its component parts, a DNA sequence encoding vde is combined in a DNA construct having, in the 5' to 3' direction of transcription, a transcription initiation control region capable of promoting transcription and translation in a host cell, the DNA sequence encoding plant vde and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having a plant vde foreign to the wild-type cell present therein, for example, by having a recombinant nucleic acid construct encoding a plant vde therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the constructs will involve regulatory regions functional in plants. The open reading frame, coding for the plant vde or functional fragment thereof will be joined at its 5' end to a transcription initiation regulatory region such as the wild-type sequence naturally found 5' upstream to the vde structural gene. Numerous other transcription initiation regions are available which provide for a wide variety of constitutive or regulatable, e.g., inducible, transcription of the structural gene functions. Constitutive promoters such as the CaMV 35S promoter, double 35S promoter, 34S figwort promoter may be useful. Promoters which express in plastid containing cells will be of special interest. Some such promoters are preferentially expressed in plastid containing tissues, such as the ssu promoter. The transcription/translation initiation regions corresponding to such structural genes are found immediately 5' upstream to the respective start codons. In embodiments wherein the expression of the vde protein is desired in a plant host, the use of all or part of the complete plant vde gene is desired; namely all or part of the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source, including the sequence encoding the plant vde of interest, or enhanced promoters, such as double 35S CAMV promoters, the sequences may be joined together using standard techniques.

Expression of the vde transcript was followed in market romaine lettuce leaves that were dark adapted for an undetermined period of time. The same level of transcript was detected in both yellow leaves and rapidly expanding green leaves. However, a greater transcript level was detected in mature green leaves. Two hybridizing transcripts were observed for each sample indicating the possibility that the upper larger transcript may be processed to the slightly smaller transcript (1.7 kb) having the greater level of hybridization. The increased level of transcript in mature green leaves of lettuce may be due to two possible reasons: higher expression occurs in tissues with a higher density of fully developed chloroplasts or expression may be regulated by light intensity since the mature green leaves receive a higher intensity of light than the immature leaves which are partially shielded in the center of the head of lettuce. Hence, use of the vde promoter may be particularly useful in the transcription of vde nucleic acid sequences or for the expression of other nucleic acid sequences of interest.

Regulatory transcript termination regions may be provided in DNA constructs of this invention as well. Transcript termination regions may be provided by the DNA sequence encoding the plant vde or a convenient transcription termination region derived from a different gene source, for example, the transcript termination region which is naturally associated with the transcript initiation region. Where the transcript termination region is from a different gene source, it will contain at least about 0.5 kb, preferably about 1–3 kb of sequence 3' to the structural gene from which the termination region is derived.

Plant expression or transcription constructs having a plant vde as the DNA sequence of interest for increased or decreased expression thereof may be employed with a wide variety of plant life, particularly, plant life where light regulation or zeaxanthin levels are important. Plants of interest include, but are not limited to ornamental plant varieties, field and forage crops, including alfalfa and trees. Depending on the method for introducing the recombinant constructs into the host cell, other DNA sequences may be required. Importantly, this invention is applicable to dicot and monocot species alike and will be readily applicable to new and/or improved transformation and regulation techniques.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to Agrobacterium infection may be successfully transformed via tripartite or binary vector methods of Agrobacterium mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region (s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations.

The invention now being generally described, it will be more readily understood by reference to the following examples which are included for purposes of illustration only and are not intended to limit the present invention.

EXAMPLES

Example 1

Lettuce vde cDNA

Vde was purified from romaine lettuce (*Lactuca sativa L. cv Romaine*) chloroplasts and peptides from a tryptic digest along with the N-terminus were sequenced (Rockholm, *Plant Physiol.* (1996) 110:697–703). Two peptides (N-terminus and tryptic fragment #15, shown in FIG. 1) were used to develop the oligonucleotides 5'-GAYGCHYTBAAGACHTGYGC-3, (SEQ ID no:8) (216-fold degeneracy) and 5'TTGVARRTTDGGRATRAT-3'(SEQ ID no:9) (144-fold degeneracy).

The partial cDNA for vde was amplified by 35 cycles of polymerase chain reaction (PCR) containing 25 pmol of each primer and lettuce cDNA using an annealing temperature of 50° C. The PCR product was subcloned into pGEM-7Zf (Promega) by blunt-end cloning and sequenced. A cDNA library was constructed from poly(A)+ RNA isolated from a pooled sample of various age romaine lettuce leaves using the Timesaver cDNA Synthesis Kit (Pharmacia) and ligated into lambda-ZAPII (Stratagene). A total of $2.5 \times 10^5$ recombinant plaques were screened with the PCR product labeled by random priming and positive clones were plaque purified followed by in vivo excision of the plasmid. The cDNAs were subcloned into the Notl site of pGEM-5Zf and both strands of cDNA were sequenced completely using an Applied Biosystems Model 373A automated sequencer. The Genbank accession number is U31462.

The vde cDNA encompasses an open reading frame encoding a 473 amino acid protein with a calculated Mr of 54,447. The deduced protein contains an 125 amino acid putative transit peptide for transport into the chloroplast lumen where the enzyme is localized (Hager, *Planta* (1969) 89:224–243). This was verified by in vitro transcription/translation of two vde (vde1:-234 to 1526 bp and vde2:-65 to 1578 bp of FIG. 1) cDNAs which produced a 55 Kd product on a sodium dodecyl sulfate (SDS)-polyacrylamide gel. The N-terminus of the mature vde protein (amino acid #126) was determined by N-terminal sequencing of purified vde from romaine lettuce. Therefore, mature vde consists of a 348 amino acid protein with a calculated Mr of 39,929 and a calculated pI of 4.57.

The primary structure of the deduced mature vde exhibits some characteristic features. The protein is hydrophilic overall with 57.2% of the total amino acid residues having polar side chains. Three interesting domains were identified in the deduced mature vde including a cysteine rich domain, a lipocalin signature and a highly charged domain. In the first domain 11 of the 13 total cysteines in the mature vde are present suggesting that this is most likely the site where dithiothreitol (DTT), a known inhibitor of vde, has its effect. The cysteines probably form more than one disulfide linkage since partial inhibition of vde activity with DTT results in an accumulation of antheraxanthin. The deduced mature vde also contains a lipocalin signature, a domain identified in a number of diverse proteins that bind small hydrophobic molecules. For example, crustacyanin, a protein from lobster carapace which contains a lipocalin signature, binds the carotenoid astaxanthin. Similarly, this domain may play a role in binding the substrate violaxanthin. In the third domain approximately 47% of the residues have charged side chains. The most striking feature of this domain is the high concentration of glutamic acid residues; 27.6% of the residues in this domain (69.2% of the total in the mature vde) are glutamic acids whereas only 2% are aspartic acids FIG. 4 provides a detailed analysis of the deduced amino acid sequence of vde. The top portion provides a comparison of the deduced amino acid sequences of vde from three plant species. The transit peptides are located in the boxed region. Identical residues are indicated by hyphens (-). Gaps introduced to maximize sequence alignment are indicated by periods (.). Asterisks (*) identify the 13 cysteine residues that are conserved between the three sequences.

The bottom map of FIG. 4 shows the three domains identified. The amino acid spanning regions for lettuce vde are indicated below the domains.

Figure 6:
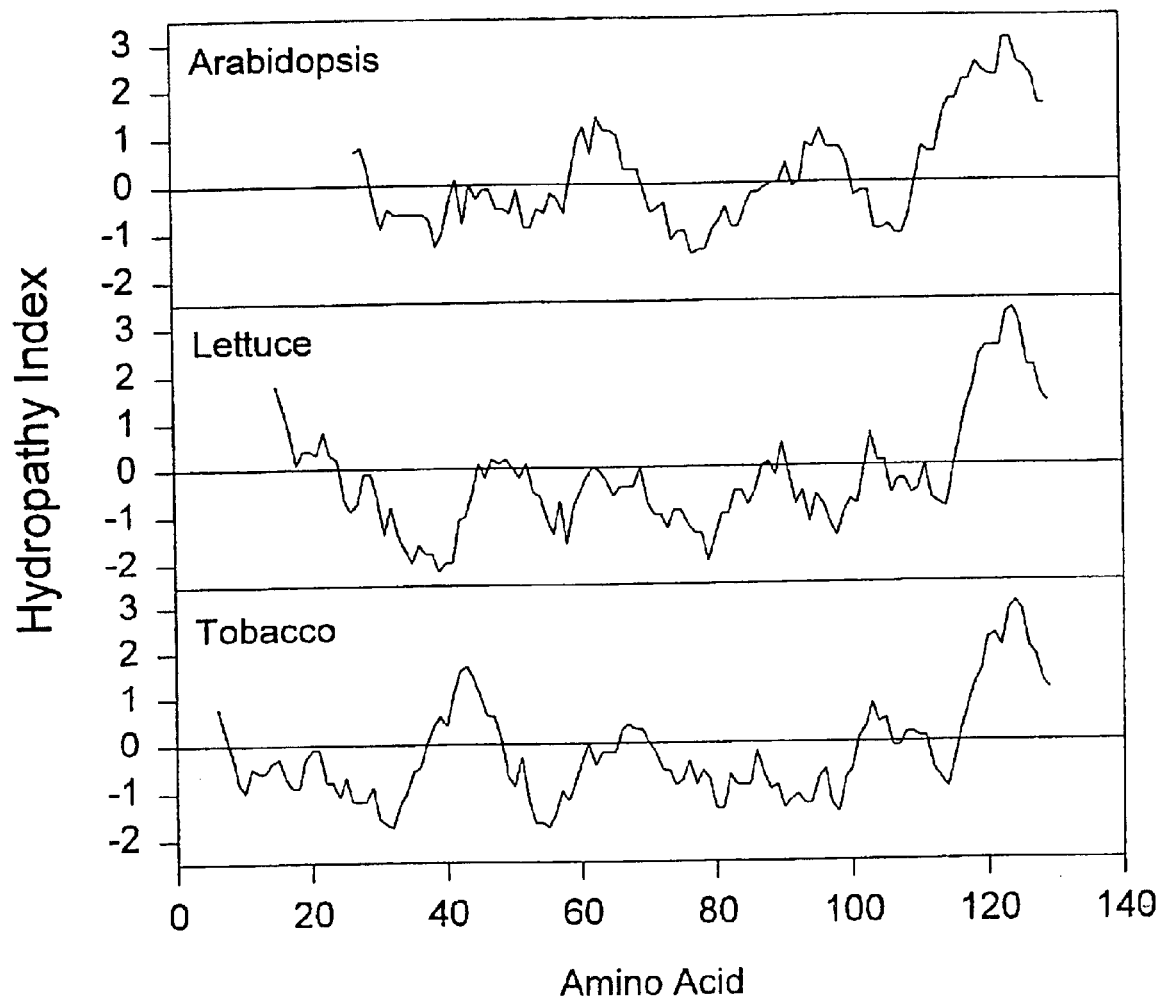
FIG. 6 provides a comparison of hyropathy profiles for the vdes of three species.

FIG. 6 provides hyropathy profiles for the vdes from three species.

Example 2

Expression of Lettuce vde cDNA in E. coli

Authenticity of the lettuce vde cDNA was confirmed by expression of the fragment vde2 in *E. coli*. Vde2 was subcloned in both sense and antisense orientations with respect to lacZ into the NotI site of pGEM-5Zf and transformed into *E. coli* DH5alpha. All cultures were incubated and induced with 10 mM IPTG (Bugos, *Plant Mol. Biol.* (1991)17:1203–1215). Following the 2 hr induction, the cells were centrifuged at 4000×g for 10 min at 4° C. The cells were resuspended in 3 ml 50 mM Tris (pH 7.4), 1 mM EDTA and lysed using an ultrasonic cell disrupter equipped with a micro-probe for 10 cycles (30 sec on/30 sec off) while being cooled in an ice bath. The resulting extract was centrifuged at 1 0.000×g for 10 min at 4° C. and the supernatant was collected for determining vde activity using the in vitro assay and absorbance change at 502 nm minus 540 nm (Yamamoto, *Methods Enzymol.* (1985) 110:303–312). The pellet was washed with 3 ml 50 mM Tris (pH 7.4), 1 mM EDTA and centrifuged. The pellet was resuspended in 3 ml buffer and assayed. All assays contained 100 μl *E. coli* extract or pellet resuspension. For quantification of xanthophyll pigments, the reactions were stopped at various times with addition of solid Tris and the xanthophylls were extracted 3 times with diethyl ether. The ether was dried under a stream of $N_2$ and the xanthophylls were solubilized in 100 μl 90% acetone followed by HPLC analysis (Gilmore, J. Chromatogr. (1991)543:137–145).

Extracts from *E. coli* expressing the fragment orientated with lacZ (sense) had strong vde activity whereas no detectable activity was observed from extracts of *E. coli* transformed with vde2 in antisense orientation or pGEM-5Zf alone. Furthermore, addition of DTT, a strong inhibitor of de-epoxidase activity, abolished all vde activity. DTT (3 mM, final conc.) was added directly to the assay 50 seconds after ascorbate (30 mM, final conc.) addition. Specific activity of the enzyme was 64.9±5.4 nmols violaxanthin deepoxidized/min/mg protein. Trace activity was detected in the membrane fraction of vde2 sense suggesting that some of the enzyme was not washed away following lysis or that lysis was not complete. An attempt to express the vde1 fragment was unsuccessful. *E. coli* transformed with vde1 subcloned in pGEM-5Zf and orientated with lacZ did not grow.

To verify the products of de-epoxidation, the reaction with vde2 sense extract was stopped at various times and the xanthophylls were analyzed by HPLC. Antheraxanthin and zeaxanthin appeared consistent with sequential de-epoxidation and concomitant with the rapid decrease in violaxanthin, similar to observations reported over three decades earlier for de-epoxidation in lima bean (*Phaseolus leunatus*) leaves exposed to high light (Yamamoto, *Arch. Biochem. Biophys.* (1962)97:168–173). The specific activity of the enzyme was 19.4±0.9 nmols violaxanthin de-epoxidized/min/mg protein. This is the first unequivocal evidence that the same enzyme catalyzes the two-step mono de-epoxidation reaction.

Example 3 vde in Other Plants

Western analysis of vde from chloroplasts of various $C_3$ plants and expressed vde in *E. coli* demonstrate that the N-terminus is conserved.

Intact chloroplasts were isolated (Neubauer, *Plant Physiol.* (1992)99:1354–1361) and lysed with five freeze/thaw cycles using liquid $N_2$ (Hager, *Planta* (1975) 88:27–44). Expression of vde2 in *E. coli* DH5-alpha was as described in Example 2 and the cells were lysed using the freeze/thaw method. Proteins were resolved on a 12% SDS-polyacrylamide gel and electrophoretically transferred to PVDF. Color development was performed following incubation with alkaline phosphatase-conjugated secondary antibodies. Protein was estimated using a prepared reagent (Biorad) and bovine gamma globulin as the standard.

The blot was probed with a polyclonal antibody prepared against a synthetic peptide derived from the N-terminus of lettuce vde (VDALKTCACLLK) (SEQ ID no:7). Vde migrates with an approximate size of 43 kD.

The mature vde from market romaine lettuce, tobacco (*Nicotiana tabacum L. cv Xanthi*) and market spinach (*Spinacia oleracea L.*) all migrate with approximately the same Mr of 43K. The antibody recognized vde in these three plant species demonstrating that the N-terminus is conserved. Expressed vde2 in *E. coli* migrated at the same Mr as the romaine lettuce vde whereas extracts from *E. coli* containing only pGEM-5Zf produce some minor cross-reacting proteins, none of which having a Mr of 43K. The Mr's of the above vde proteins are in agreement with the calculated Mr of the deduced mature vde (39.9K). Two interesting observations are evident from vde expressed in *E. coli*. The first is that the *E. coli* expressed vde produced many immunoreactive bands of lower molecular weight. Reasons for this may be due to some processing occurring at the C-terminus of the protein by *E. coli* (since the antibody recognizes the N-terminus) or due to translational pausing. The second is that the bacterial expressed vde protein migrates at the same molecular weight as mature vde from romaine lettuce and not as the expected size of the deduced vde preprotein (54.4K) with the transit peptide. This suggests that *E. coli* may recognize the chloroplast transit peptide and cleave it. The N-terminus of the bacterial expressed vde will need to be sequenced to determine the actual site where cleavage is occurring. A similar observation was also reported for the nuclear-encoded chloroplast enzyme acetolactate synthase from *Arabidopsis* when expressed in *E. coli*.

Figure 7B:
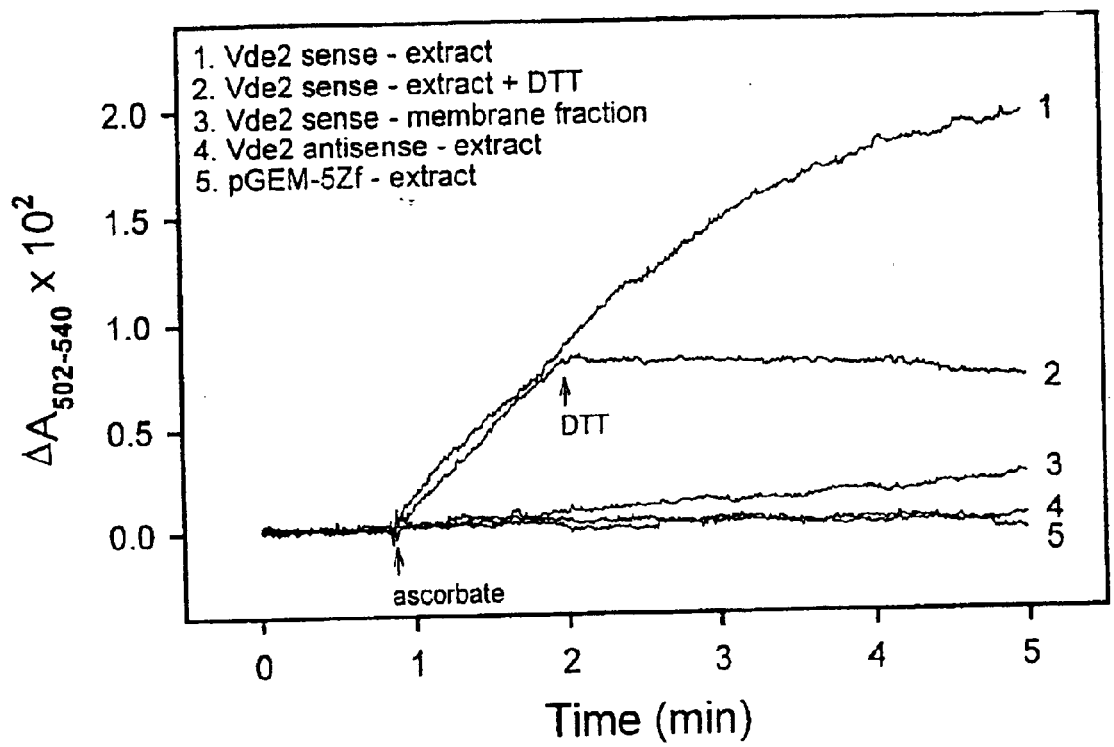
FIG. 7 provides a time-course comparison of effects of expressed vde.
Figure 7A:
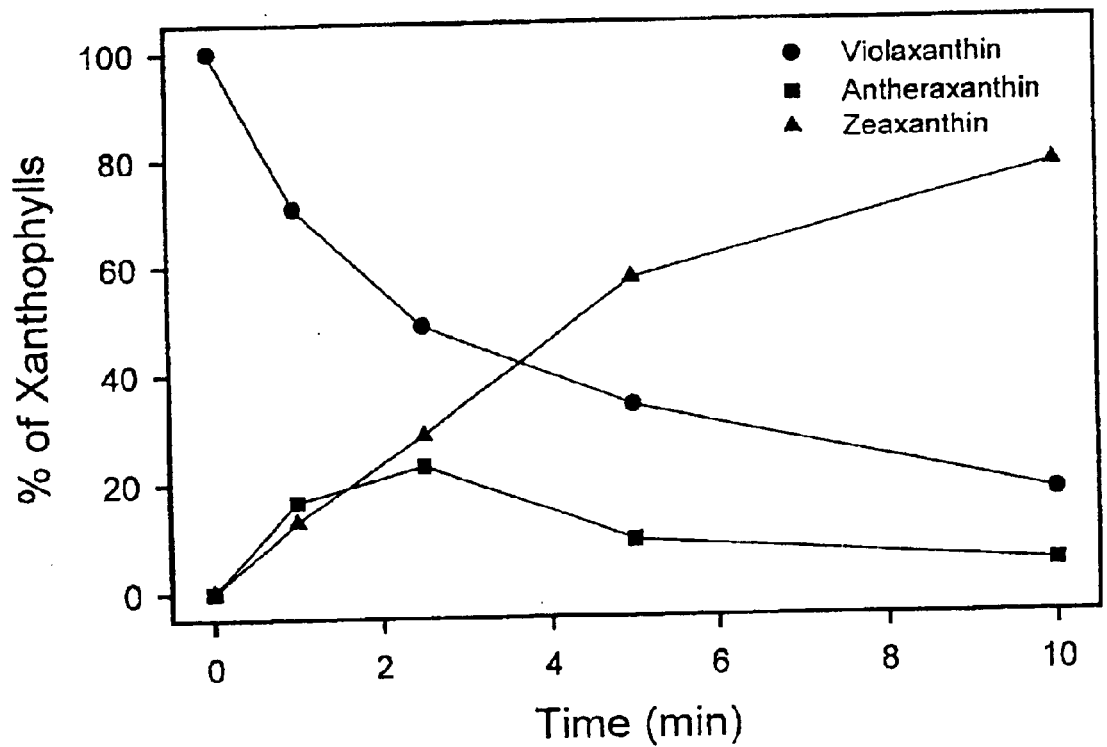

FIG. 7 shows the kinetics of absorbance change demonstrating expression of active violaxanthin de-epoxidase in *E. coli* DH5 (top of FIG. 7). Expression was assayed from vde2 constructs in both sense and antisense orientations with respect to lacz along with *E. coli* containing the vector only (pGEM-5Zf). DTT (3 mM, final concentration) was added directly to the assay 70 seconds after ascorbate (30 mM, final concentration) additioin. Specific activity of the enzyme was 64.9±5.4 nmols violaxanthin de-epoxidized min–1 mg. protein–1. The bottom of FIG. 7 is a timecourse of xanthophyll conversions by expressed vde2 (sense construct) in *E. coli*. Specific activity of the enzyme was 19.4±0.9 nmols violaxanthin de-epoxidized min–1 protein–1.

Example 4

Effects of Expression of vde in Plants

In FIG. 8, pigment analysis of leaves of 212 control tobacco plants (Ct-#) is provided, as well as the mean percentage of violaxanthin which is de-epoxidized. Also provided by FIG. 8 is the pigment analysis of leaves of 18 vde-antisense tobacco plants (TAS-#).

Tobacco plants were transformed with an antisense construct of the tobacco vde cDNA under control of the CaMV 35S promoter (pB1121) using *Agrobacterium tumefaciens* LBA4404. A total of 40 antisense plants were analyzed with 18 showing various levels of inhibition of de-epoxidation.

Relative pigment concentration for tobacco (*Nicotiana tabacum L. cv. Xanthi*) leaves was measured by leaf disks punched from tobacco leaves that were dark adapted for a few hours. One leaf disk (dark adapted) was extracted with acetone and analyzed by HPLC while another was light induced by exposing the disk to 1800 mmol m–2 s–1 white light for 20 min while the leaf disk was floating on water in a water-jacketed beaker cooled at 20_C. Following the light treatment, the leaf disk was extracted and analyzed by HPLC.

Two vde-antisense tobacco plants (TAS-32 and TAS-39) were recovered that had undetectable levels of zeaxanthin following illumination with bright white light. Low levels of antheraxanthin (~2–3%) were present in some dark-adapted leaves and are assumed to represent incomplete epoxidase activity.

Figure 9:
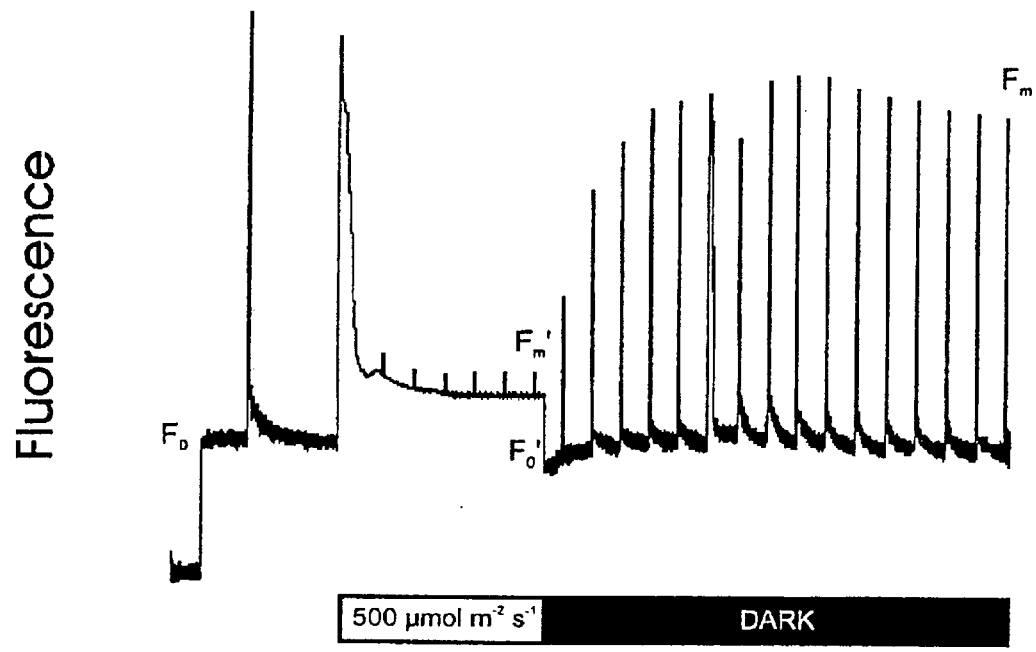
FIG. 9 shows the results of a control plant extraction for vde.
Figure 10:
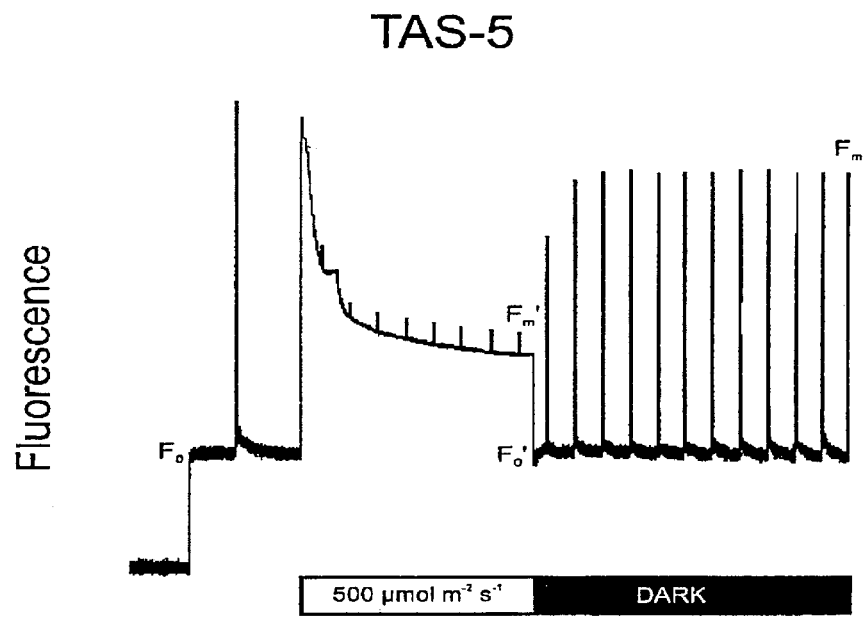
FIG. 10 shows the results of extraction for vde in an antisense vde plant.

In FIGS. 9 and 10, results are provided from a comparison of measurements on a tobacco leaf from a control plant (Ct-30) and a vde-antisense plant (TAS-5), both of which were dark adapted for 24 hours. Under low light conditions, three leaf disks were punched from each leaf. One leaf disk (dark adapted) was extracted and analyzed by HPLC.

The remaining two leaf disks were pre-illuminated with 500 mmol m–2 s–1 red light for 15 minutes. One of these disks was then extracted and analyzed by HPLC while the other was placed in the dark for 10 minutes prior to fluorometry and HPLC analysis.

It has also been observed that in tobacco plants where lettuce vde has been overexpressed from a 35S construct, flowering is delayed, and flowers are slightly larger.

SEQUENCE LISTING

<160> NUMBER OF SEQ ID NOS: 9

<210> SEQ ID NO 1
<211> LENGTH: 1981
<212> TYPE: DNA
<213> ORGANISM: Lactuca sativa

<400> SEQUENCE: 1

```
tgtgggttcg aattttaccc accacaagtt ttgtcctacc ataattggga taaggagtct      60
aatttccctt gtacaatttt ccaatttctt cctccgccac accatatata tactgtacgc     120
cacttcgaac gctacaatgt ttgaaaaaag acgcagattt tacaaagacg gagaagataa     180
taagcttcaa gtactccgat cgtcaggtgg cctttggaag ccaacaaact ggctatggct     240
ctttctcttc acactgtatt tctctgcaaa gaggaagccc tcaatttata tgcaagatca     300
ccatgtaatg aaaggtttca caggagtgga caacctccta ccaacataat catgatgaaa     360
attcgatcca acaatggata ttttaattct ttccggttgt ttacatctta taagacaagt     420
tctttctcag attctagcca ttgcaaggat aaatctcaga tatgcagcat cgatacaagt     480
tttgaggaaa tacaaagatt tgatctcaaa aggggcatga ctttgattct tgaaaagcaa     540
```

```
tggagacaat tcatacaatt ggctatcgta ttggtttgca catttgttat cgttcccaga      600
gttgatgccg ttgatgctct taaaacttgt gcttgtttac tcaaagaatg caggattgag      660
cttgcaaaat gtatagcaaa cccatcttgt gcggcaaacg ttgcctgtct acagacttgc      720
aacaatcgtc ctgacgagac cgaatgtcag ataaaatgtg gtgacttgtt cgaaaacagt      780
gtggtggacc aattcaacga gtgtgcggtt tcccgaaaga aatgtgtgcc ccggaaatcg      840
gatgtgggtg aattcccggt tccggatcgt aatgcagtgg ttcaaaattt taacatgaaa      900
gactttagtg ggaagtggta tataacaagt ggtttaaatc ctacatttga tgcatttgat      960
tgtcaacttc atgagtttca tatggaaaat gataaacttg ttgggaactt aacatggcgc     1020
ataaaaactt tggatggtgg tttctttact cgatctgctg tgcaaacatt tgttcaagat     1080
ccagatcttc ctggagcact ttataatcat gacaatgagt tcttcacta ccaagatgac      1140 tggtacatat tatcttccca aatcgaaaac aaacccgatg attacatatt cgtatactac     1200
cgaggtcgaa acgacgcatg ggatggatac ggtgggtccg tgatctacac ccgaagcccg     1260
acactccccg aatcgatcat cccaaaccta caaaaagcag ccaaatccgt gggtcgagac     1320
tttaacaatt tcataacaac cgacaatagt tgtgggcctg agcctccatt ggtggaaagg     1380
cttgagaaaa cagcggaaga gggcgagaag ttgttgataa agaagctgt agagatagaa      1440 gaagaggttg aaaagaggt ggagaaggtt agagatactg agatgacttt gtttcagagg      1500
ttgcttgaag ggtttaagga gttgcaacaa gatgaagaga attttgtgag ggagttgagt     1560
aaagaagaga aggaaattct gaatgaactt caaatggaag cgactgaagt tgaaaagctt     1620
tttgggcgcg cgttaccgat taggaaactt agataaattt cgatgattga ttcagacaat     1680
atatatagtc atatggatta tgtagatact agagaaaacc caaaaaaact tttgtatacg     1740
tgataaacgt gttttgtgatt tgtttattgg cttaaaattg tagaatagct tttttaattc     1800
tttacaaaaa aattgattgt ctattggtag ccaagaggtt cacgaaaaga ctgaaagggt     1860
cttgccggtt tgcgggttag gccaaatttt ttggggcggg atcggtcttg atcgggtttt     1920
tctttaaaac atgtattttt tataaatgat gagttatttt caattttgg ctaaaaaaaa      1980 a                                                                     1981
```

<210> SEQ ID NO 2
<211> LENGTH: 473
<212> TYPE: PRT
<213> ORGANISM: Lactuca sativa

<400> SEQUENCE: 2

```
Met Ala Leu Ser Leu His Thr Val Phe Leu Cys Lys Glu Glu Ala Leu
1               5                   10                  15

Asn Leu Tyr Ala Arg Ser Pro Cys Asn Glu Arg Phe His Arg Ser Gly
            20                  25                  30

Gln Pro Pro Thr Asn Ile Ile Met Met Lys Ile Arg Ser Asn Asn Gly
        35                  40                  45

Tyr Phe Asn Ser Phe Arg Leu Phe Thr Ser Tyr Lys Thr Ser Ser Phe
    50                  55                  60

Ser Asp Ser Ser His Cys Lys Asp Lys Ser Gln Ile Cys Ser Ile Asp
65                  70                  75                  80

Thr Ser Phe Glu Glu Ile Gln Arg Phe Asp Leu Lys Arg Gly Met Thr
                85                  90                  95

Leu Ile Leu Glu Lys Gln Trp Arg Gln Phe Ile Gln Leu Ala Ile Val
            100                 105                 110
```

Leu Val Cys Thr Phe Val Ile Val Pro Arg Val Asp Ala Val Asp Ala
            115                 120                 125

Leu Lys Thr Cys Ala Cys Leu Leu Lys Glu Cys Arg Ile Glu Leu Ala
    130                 135                 140

Lys Cys Ile Ala Asn Pro Ser Cys Ala Ala Asn Val Ala Cys Leu Gln
145                 150                 155                 160

Thr Cys Asn Asn Arg Pro Asp Glu Thr Glu Cys Gln Ile Lys Cys Gly
                165                 170                 175

Asp Leu Phe Glu Asn Ser Val Val Asp Gln Phe Asn Glu Cys Ala Val
            180                 185                 190

Ser Arg Lys Lys Cys Val Pro Arg Lys Ser Asp Val Gly Glu Phe Pro
        195                 200                 205

Val Pro Asp Arg Asn Ala Val Val Gln Asn Phe Asn Met Lys Asp Phe
    210                 215                 220

Ser Gly Lys Trp Tyr Ile Thr Ser Gly Leu Asn Pro Thr Phe Asp Ala
225                 230                 235                 240

Phe Asp Cys Gln Leu His Glu Phe His Met Glu Asn Asp Lys Leu Val
                245                 250                 255

Gly Asn Leu Thr Trp Arg Ile Lys Thr Leu Asp Gly Gly Phe Phe Thr
            260                 265                 270

Arg Ser Ala Val Gln Thr Phe Val Gln Asp Pro Asp Leu Pro Gly Ala
        275                 280                 285

Leu Tyr Asn His Asp Asn Glu Phe Leu His Tyr Gln Asp Asp Trp Tyr
    290                 295                 300

Ile Leu Ser Ser Gln Ile Glu Asn Lys Pro Asp Asp Tyr Ile Phe Val
305                 310                 315                 320

Tyr Tyr Arg Gly Arg Asn Asp Ala Trp Asp Gly Tyr Gly Gly Ser Val
                325                 330                 335

Ile Tyr Thr Arg Ser Pro Thr Leu Pro Glu Ser Ile Ile Pro Asn Leu
            340                 345                 350

Gln Lys Ala Ala Lys Ser Val Gly Arg Asp Phe Asn Asn Phe Ile Thr
        355                 360                 365

Thr Asp Asn Ser Cys Gly Pro Glu Pro Pro Leu Val Glu Arg Leu Glu
370                 375                 380

Lys Thr Ala Glu Glu Gly Glu Lys Leu Leu Ile Lys Glu Ala Val Glu
385                 390                 395                 400

Ile Glu Glu Glu Val Glu Lys Glu Val Glu Lys Val Arg Asp Thr Glu
                405                 410                 415

Met Thr Leu Phe Gln Arg Leu Leu Glu Gly Phe Lys Glu Leu Gln Gln
            420                 425                 430

Asp Glu Glu Asn Phe Val Arg Glu Leu Ser Lys Glu Glu Lys Glu Ile
        435                 440                 445

Leu Asn Glu Leu Gln Met Glu Ala Thr Glu Val Glu Lys Leu Phe Gly
    450                 455                 460

Arg Ala Leu Pro Ile Arg Lys Leu Arg
465                 470

<210> SEQ ID NO 3
<211> LENGTH: 1589
<212> TYPE: DNA
<213> ORGANISM: Nicotiana tabacum

<400> SEQUENCE: 3
tattttcatg agtttgcagt tggtggtaat acggttgaag aatggctctt gccctcatt    60

-continued

```
caaattttct ggccaaccat gaaaccatca aatattatgt tgggtcaaag cttcccggtc    120
ataaaaggtt tagctggggt tgggaagatt actttggtag tatagtcgta gcaaaaattt    180
gttccagcag acggatacct agatactttc gaaaatctcc tagaatatgc tgtggtttgg    240
attcaagagg tctgcaacta ttctcacacg ggaaacacaa tctctctccc gcacatagca    300
ttaaccagaa tgtacctaag ggaaattcag gatgcaaatt tccaaaagat gtagctttga    360
tggtttggga gaaatggggc caatttgcca aaacagcaat gtagctata ttcattttgt     420
cagttgcttc aaaagctgat gcggttgatg ctctcaagac ttgtacttgc ttactgaaag    480
agtgcaggtt agagcttgcg aagtgcattt cgaaccctgc atgtgcagct aatgttgcct    540
gtctccagac ttgcaacaat agacctgacg aaacggaatg tcagataaaa tgtggtgatt    600
tgtttgaaaa cagtgtcgta gacgagttca atgagtgtgc agtctcccga agaaatgtg    660
tacctcgtaa atctgatgtt ggtgactttc ctgtacctga tcccagtgtt cttgtccaga    720
agtttgacat gaaagatttt agcgggaaat ggttcattac tcgcggtttg aatcccactt    780
ttgatgcttt tgattgccaa ttgcatgagt tccatacaga agaaaacaaa cttgtgggga    840
atttatcttg gagaatacgt acacctgatg gaggattttt tactcgatca gcggtgcaaa    900
aattcgtgca agatccaaag tatccgggga tactctacaa tcatgataat gagtatcttc    960
tctaccaaga tgactggtat attttgtcat ccaaagtaga aaatagtcca gaggattaca   1020
tatttgtgta ctataagggc agaaatgatg catgggatgg atatggtggt tctgtacttt   1080
acacaagaag tgcagttttg cctgaaagca ttataccgga gttgcaaacc gcagctcaaa   1140
aagttgggcg tgatttcaac acattcataa aaacagacaa tacatgtggc cctgaacctc   1200
cccttgttga gaggttggag aagaaagtgg aagaaggaga aaggacgatc ataaaagaag   1260
ttgaggagat agaagaagaa gtagagaagg tgagagataa agaagtcacc ttattcagta   1320
aactgtttga aggttttaaa gagctccaac gagatgaaga gaacttctta agagagctga   1380
gcaaagaaga aatggatgtt ttggatggac ttaaaatgga agcaactgag gtagaaaaac   1440
ttttttgggcg tgctttacca ataaggaaat taaggtaagt attttaaaa ctatcaacat    1500
atatactaca tgtatagttg tatttgattc ttttgcctgg aatagattgc ttatacatca   1560
tgtattgctt cttttcaga agcaaaaaa                                      1589
```

<210> SEQ ID NO 4
<211> LENGTH: 477
<212> TYPE: PRT
<213> ORGANISM: Nicotiana tabacum

<400> SEQUENCE: 4

```
Met Ala Leu Ala Pro His Ser Asn Phe Leu Ala Asn His Glu Thr Ile
1               5                   10                  15

Lys Tyr Tyr Val Gly Ser Lys Leu Pro Gly His Lys Arg Phe Ser Trp
            20                  25                  30

Gly Trp Glu Asp Tyr Phe Gly Ser Ile Val Val Ala Lys Ile Cys Ser
        35                  40                  45

Ser Arg Arg Ile Pro Arg Tyr Phe Arg Lys Ser Pro Arg Ile Cys Cys
    50                  55                  60

Gly Leu Asp Ser Arg Gly Leu Gln Leu Phe Ser His Gly Lys His Asn
65                  70                  75                  80

Leu Ser Pro Ala His Ser Ile Asn Gln Asn Val Pro Lys Gly Asn Ser
                85                  90                  95

Gly Cys Lys Phe Pro Lys Asp Val Ala Leu Met Val Trp Glu Lys Trp
```

```
                100               105                110
Gly Gln Phe Ala Lys Thr Ala Ile Val Ala Ile Phe Ile Leu Ser Val
            115                 120                 125
Ala Ser Lys Ala Asp Ala Val Asp Ala Leu Lys Thr Cys Thr Cys Leu
130                 135                 140
Leu Lys Glu Cys Arg Leu Glu Leu Ala Lys Cys Ile Ser Asn Pro Ala
145                 150                 155                 160
Cys Ala Ala Asn Val Ala Cys Leu Gln Thr Cys Asn Asn Arg Pro Asp
                165                 170                 175
Glu Thr Glu Cys Gln Ile Lys Cys Gly Asp Leu Phe Glu Asn Ser Val
            180                 185                 190
Val Asp Glu Phe Asn Glu Cys Ala Val Ser Arg Lys Lys Cys Val Pro
            195                 200                 205
Arg Lys Ser Asp Val Gly Asp Phe Pro Val Pro Asp Pro Ser Val Leu
            210                 215                 220
Val Gln Lys Phe Asp Met Lys Asp Phe Ser Gly Lys Trp Phe Ile Thr
225                 230                 235                 240
Arg Gly Leu Asn Pro Thr Phe Asp Ala Phe Asp Cys Gln Leu His Glu
                245                 250                 255
Phe His Thr Glu Glu Asn Lys Leu Val Gly Asn Leu Ser Trp Arg Ile
                260                 265                 270
Arg Thr Pro Asp Gly Gly Phe Thr Arg Ser Ala Val Gln Lys Phe
            275                 280                 285
Val Gln Asp Pro Lys Tyr Pro Gly Ile Leu Tyr Asn His Asp Asn Glu
            290                 295                 300
Tyr Leu Leu Tyr Gln Asp Asp Trp Tyr Ile Leu Ser Ser Lys Val Glu
305                 310                 315                 320
Asn Ser Pro Glu Asp Tyr Ile Phe Val Tyr Tyr Lys Gly Arg Asn Asp
                325                 330                 335
Ala Trp Asp Gly Tyr Gly Gly Ser Val Leu Tyr Thr Arg Ser Ala Val
            340                 345                 350
Leu Pro Glu Ser Ile Ile Pro Glu Leu Gln Thr Ala Ala Gln Lys Val
            355                 360                 365
Gly Arg Asp Phe Asn Thr Phe Ile Lys Thr Asp Asn Thr Cys Gly Pro
370                 375                 380
Glu Pro Pro Leu Val Glu Arg Leu Glu Lys Lys Val Glu Glu Gly Glu
385                 390                 395                 400
Arg Thr Ile Ile Lys Glu Val Glu Glu Ile Glu Glu Val Glu Lys
                405                 410                 415
Val Arg Asp Lys Glu Val Thr Leu Phe Ser Lys Leu Phe Glu Gly Phe
            420                 425                 430
Lys Glu Leu Gln Arg Asp Glu Asn Phe Leu Arg Glu Leu Ser Lys
            435                 440                 445
Glu Glu Met Asp Val Leu Asp Gly Leu Lys Met Glu Ala Thr Glu Val
            450                 455                 460
Glu Lys Leu Phe Gly Arg Ala Leu Pro Ile Arg Lys Leu
465                 470                 475

<210> SEQ ID NO 5
<211> LENGTH: 1555
<212> TYPE: DNA
<213> ORGANISM: Arabidopsis thaliana

<400> SEQUENCE: 5
```

-continued

```
ccacgcgtcc ggcttggtgt ggggaagatt agatagtgtg aagaatggca gtagctacac      60
attgtttcac ttcaccttgt catgaccgta ttcgattttt ctcaagtgat gatggtattg     120
gtaggcttgg cattacaaga aagaggatca atggcacttt cttgctcaag attttacctc     180
caatccaaag tgctgatctc agaacaactg gtgggagatc tcacgtcct ttatctgcat      240
tcaggtcagg attctctaag gggatatttg acattgtgcc attaccatca agaatgagc      300
tgaaagagct gaccgctccg ctgttgctaa aactcgtggg tgttttagct tgcgcgttcc     360
ttattgttcc atctgcagat gcagttgatg cacttaaaac ttgtgcatgc ttattgaagg     420
gatgcaggat agaactcgca aagtgcattg ccaaccctgc ctgtgcagcc aatgtcgcgt     480
gccttcagac ctgcaataac cgtccagatg aaaccgagtg ccagattaaa tgtggggatc     540
tgtttgagaa cagtgttgtt gatgagttca acgagtgtgc tgtgtcgaga aaaaagtgtg     600
ttcctagaaa atctgatctc ggagaatttc ctgccccaga cccttctgtt cttgtacaga     660
acttcaacat ctcggacttt aacgggaagt ggtacattac aagtggcttg aatccaacct     720
ttgatgcctt cgactgccag ctgcatgagt tccacacaga aggtgacaac aagcttgttg     780
gaaacatctc ttggagaata aagaccctag acagtggatt cttttactag gtcagccgtac    840
aaaaattcgt gcaagatcct aaccaacctg gtgttctcta caatcatgac aacgagtacc     900
ttcactatca agatgactgg tatatcctgt catcaaagat agagaataaa cctgaagact     960
atatatttgt atactaccgt gggcgaaacg atgcttggga tggatatggt ggtgcagttg    1020
tatacacgag aagttctgta ttacccaata gcattatacc agaactcgaa aaagcagcaa    1080
aaagcatagg cagagacttc agcacattca ttagaacgga taacacatgt ggtcctgaac    1140
ctgcgctcgt ggagagaatt gagaagacag tggaagaagg tgaaaggata atcgtaaaag    1200
aggttgaaga gatagaagaa gaggtagaga aggaagtgga gaaggtcggt aggactgaga    1260
tgaccttgtt ccagagattg gctgaaggat ttaatgaact gaagcaagac gaggagaatt    1320
tcgtgagaga gttaagtaaa gagagatgg agttttggga tgagatcaaa atggaagcaa     1380
gtgaggttga aaaattgttt gggaaagctt tgccaatcag gaaggtcagg tagaaacaag    1440
aaccaccatt gttgtacaaa ctatattata catactgtgt tcggttcata taagtaata     1500
tttttgtaca cagtcatcat cattccataa caattggata aaaaaaaaaa aaaaa          1555
```

<210> SEQ ID NO 6
<211> LENGTH: 462
<212> TYPE: PRT
<213> ORGANISM: Arabidopsis thaliana

<400> SEQUENCE: 6

```
Met Ala Val Ala Thr His Cys Phe Thr Ser Pro Cys His Asp Arg Ile
1               5                   10                  15

Arg Phe Phe Ser Ser Asp Asp Gly Ile Gly Arg Leu Gly Ile Thr Arg
            20                  25                  30

Lys Arg Ile Asn Gly Thr Phe Leu Leu Lys Ile Leu Pro Pro Ile Gln
        35                  40                  45

Ser Ala Asp Leu Arg Thr Thr Gly Gly Arg Ser Ser Arg Pro Leu Ser
    50                  55                  60

Ala Phe Arg Ser Gly Phe Ser Lys Gly Ile Phe Asp Ile Val Pro Leu
65                  70                  75                  80

Pro Ser Lys Asn Glu Leu Lys Glu Leu Thr Ala Pro Leu Leu Lys
            85                  90                  95

Leu Val Gly Val Leu Ala Cys Ala Phe Leu Ile Val Pro Ser Ala Asp
```

```
                100                 105                 110
Ala Val Asp Ala Leu Lys Thr Cys Ala Cys Leu Leu Lys Gly Cys Arg
            115                 120                 125

Ile Glu Leu Ala Lys Cys Ile Ala Asn Pro Ala Cys Ala Ala Asn Val
        130                 135                 140

Ala Cys Leu Gln Thr Cys Asn Asn Arg Pro Asp Glu Thr Glu Cys Gln
145                 150                 155                 160

Ile Lys Cys Gly Asp Leu Phe Glu Asn Ser Val Val Asp Glu Phe Asn
                165                 170                 175

Glu Cys Ala Val Ser Arg Lys Lys Cys Val Pro Arg Lys Ser Asp Leu
            180                 185                 190

Gly Glu Phe Pro Ala Pro Asp Pro Ser Val Leu Val Gln Asn Phe Asn
        195                 200                 205

Ile Ser Asp Phe Asn Gly Lys Trp Tyr Ile Thr Ser Gly Leu Asn Pro
210                 215                 220

Thr Phe Asp Ala Phe Asp Cys Gln Leu His Glu Phe His Thr Glu Gly
225                 230                 235                 240

Asp Asn Lys Leu Val Gly Asn Ile Ser Trp Arg Ile Lys Thr Leu Asp
                245                 250                 255

Ser Gly Phe Phe Thr Arg Ser Ala Val Gln Lys Phe Val Gln Asp Pro
            260                 265                 270

Asn Gln Pro Gly Val Leu Tyr Asn His Asp Asn Glu Tyr Leu His Tyr
        275                 280                 285

Gln Asp Asp Trp Tyr Ile Leu Ser Ser Lys Ile Glu Asn Lys Pro Glu
    290                 295                 300

Asp Tyr Ile Phe Val Tyr Tyr Arg Gly Arg Asn Asp Ala Trp Asp Gly
305                 310                 315                 320

Tyr Gly Gly Ala Val Val Tyr Thr Arg Ser Ser Val Leu Pro Asn Ser
                325                 330                 335

Ile Ile Pro Glu Leu Glu Lys Ala Ala Lys Ser Ile Gly Arg Asp Phe
            340                 345                 350

Ser Thr Phe Ile Arg Thr Asp Asn Thr Cys Gly Pro Glu Pro Ala Leu
        355                 360                 365

Val Glu Arg Ile Glu Lys Thr Val Glu Glu Gly Glu Arg Ile Ile Val
    370                 375                 380

Lys Glu Val Glu Glu Ile Glu Glu Val Glu Lys Glu Val Glu Lys
385                 390                 395                 400

Val Gly Arg Thr Glu Met Thr Leu Phe Gln Arg Leu Ala Glu Gly Phe
                405                 410                 415

Asn Glu Leu Lys Gln Asp Glu Glu Asn Phe Val Arg Glu Leu Ser Lys
            420                 425                 430

Glu Glu Met Glu Phe Leu Asp Glu Ile Lys Met Glu Ala Ser Glu Val
        435                 440                 445

Glu Lys Leu Phe Gly Lys Ala Leu Pro Ile Arg Lys Val Arg
    450                 455                 460

<210> SEQ ID NO 7
<211> LENGTH: 12
<212> TYPE: PRT
<213> ORGANISM: Artificial
<220> FEATURE:
<223> OTHER INFORMATION: synthetic peptide derived from the N-terminus
      of lettuce vde
<220> FEATURE:
<221> NAME/KEY: MISC_FEATURE
<222> LOCATION: (1)..(12)
```

-continued

```
<223> OTHER INFORMATION: Synthetic peptide derived from the N-terminus
      of lettuce vde

<400> SEQUENCE: 7

Val Asp Ala Leu Lys Thr Cys Ala Cys Leu Leu Lys
1               5                   10

<210> SEQ ID NO 8
<211> LENGTH: 20
<212> TYPE: DNA
<213> ORGANISM: Artificial
<220> FEATURE:
<223> OTHER INFORMATION: synthetic oligonucleotide

<400> SEQUENCE: 8
gaygchytba agachtgygc                                              20

<210> SEQ ID NO 9
<211> LENGTH: 18
<212> TYPE: DNA
<213> ORGANISM: Artificial
<220> FEATURE:
<223> OTHER INFORMATION: synthetic oligonucleotide

<400> SEQUENCE: 9
ttgvarrttd ggratrat                                                18
```

What is claimed is:

1. A method of producing a transformed plant with a modified level of zeaxanthin comprising growing a plant transformed with a construct comprising, in the order of transcription, a plant transcription initiation region, a DNA sequence encoding a plant violaxanthin de-epoxidase, and a transcriptional termination region, wherein said promoter sequence is heterologous to said DNA sequence and wherein the DNA sequence encoding a plant violaxanthin de-epoxidase is selected from the group consisting of SEQ ID NO: 1, SEQ ID NO:3, and SEQ ID NO:5.

2. A plant produced by the method of claim 1.

* * * * *